US007807155B2

(12) United States Patent
Di Padova et al.

(10) Patent No.: US 7,807,155 B2
(45) Date of Patent: Oct. 5, 2010

(54) IL-17 ANTAGONISTIC ANTIBODIES

(75) Inventors: Franco E. Di Padova, Birsfelden (CH); Hermann Gram, Weil am Rhein (DE); Hans Hofstetter, Riehen (CH); Margit Jeschke, Basel (CH); Jean-Michel Rondeau, Rixheim (FR); Wim Van Den Berg, Molenhoek (NL)

(73) Assignee: Novartis AG, Basel (CH)

( * ) Notice: Subject to any disclaimer, the term of this patent is extended or adjusted under 35 U.S.C. 154(b) by 637 days.

(21) Appl. No.: 11/658,344

(22) PCT Filed: Aug. 4, 2005

(86) PCT No.: PCT/EP2005/008470

§ 371 (c)(1),
(2), (4) Date: Mar. 2, 2007

(87) PCT Pub. No.: WO2006/013107

PCT Pub. Date: Feb. 9, 2006

(65) Prior Publication Data

US 2009/0280131 A1 Nov. 12, 2009

(30) Foreign Application Priority Data

Aug. 5, 2004 (GB) .................. 0417487.6

(51) Int. Cl.
*A61K 39/395* (2006.01)
*C07K 16/46* (2006.01)
*C07K 16/24* (2006.01)
*C12P 21/08* (2006.01)

(52) U.S. Cl. ............ 424/130.1; 530/387.9; 530/388.23; 530/350; 435/69.5; 435/326; 536/23.5

(58) Field of Classification Search ................ None
See application file for complete search history.

(56) References Cited

U.S. PATENT DOCUMENTS

| 5,869,286 | A | 2/1999 | Yao et al. | |
| 6,043,344 | A | 3/2000 | Jacobs et al. | |
| 6,072,033 | A | 6/2000 | Yao et al. | |
| 6,072,037 | A | 6/2000 | Yao et al. | |
| 6,074,849 | A | 6/2000 | Jacobs et al. | |
| 6,096,305 | A | 8/2000 | Yao et al. | |
| 6,100,235 | A | 8/2000 | Yao et al. | |
| 6,274,711 | B1 | 8/2001 | Golstein et al. | |
| 6,562,578 | B1 | 5/2003 | Gorman | |
| 7,193,064 | B2 * | 3/2007 | Mikayama et al. | 530/388.73 |
| 7,456,264 | B2 * | 11/2008 | Keler et al. | 530/388.4 |
| 2003/0223996 | A1 | 12/2003 | Ruben et al. | |

FOREIGN PATENT DOCUMENTS

| DE | 29820466 U1 | 5/1999 |
| EP | 1053751 | 11/2000 |
| EP | 1933869 | 10/2009 |
| JP | 2000186046 | 7/2000 |
| WO | 95/18826 | 7/1995 |
| WO | 96/29408 | 9/1996 |
| WO | 97/04097 | 2/1997 |
| WO | 97/15320 | 5/1997 |
| WO | 98/23284 | 6/1998 |
| WO | 99/14240 | 3/1999 |
| WO | 99/24077 | 5/1999 |
| WO | 99/32632 | 7/1999 |
| WO | 99/35263 | 7/1999 |
| WO | 99/35267 | 7/1999 |
| WO | 99/41368 | 8/1999 |
| WO | 99/41369 | 8/1999 |
| WO | 99/41402 | 8/1999 |
| WO | 99/60127 | 11/1999 |
| WO | 00/15759 | 3/2000 |
| WO | 00/15798 | 3/2000 |
| WO | 00/20593 | 4/2000 |
| WO | 00/22909 | 4/2000 |
| WO | 00/29582 | 5/2000 |
| WO | 00/42187 | 7/2000 |
| WO | 00/42188 | 7/2000 |
| WO | 00/44349 | 8/2000 |
| WO | 00/47228 | 8/2000 |
| WO | 00/55204 | 9/2000 |
| WO | 00/69463 | 11/2000 |
| WO | 01/15728 | 3/2001 |
| WO | WO 02/02641 | 1/2002 |
| WO | 02/33083 | 4/2002 |

(Continued)

OTHER PUBLICATIONS

Hwang et al, Arthritis Research and Therapy, 2004, vol. 6, No. 2, pp. R120-R127.*
R&D Systems: "Monoclonal Anti-human IL-17 Antibody", R&D Systems Catalogue, 'Online, Jan. 11, 2004.
Chabaud M et al., "Contribution of Interleukin 17 to Synovium Matrix Destruction in Rheumatoid Arthritis", Cytokine, Academic Press LTD, Philadelphia, PA, vol. 12, No. 7, pp. 1092-1090, (2000).
Database WPI, Section Ch, Week 200051, Derwent Publications Ltd., London, GB, AN 2000-551579, Jul. 4, 2000.

(Continued)

*Primary Examiner*—Bridget E Bunner
*Assistant Examiner*—Fozia M Hamud
(74) *Attorney, Agent, or Firm*—Leslie Fischer

(57) ABSTRACT

An IL-17 binding molecule, in particular an antibody to human IL-17, more preferably a human antibody to human IL-17 is provided, wherein the hypervariable regions of the heavy and light chains have amino acid sequences as defined, for use in the treatment of an IL-17 mediated disease or disorder, e.g. rheumatoid arthritis.

22 Claims, 2 Drawing Sheets

FOREIGN PATENT DOCUMENTS

| WO | 02/058717 | 8/2002 |
|---|---|---|
| WO | 02/102411 | 12/2002 |
| WO | WO02/102411 | 12/2002 |
| WO | WO 03/055979 | 7/2003 |

OTHER PUBLICATIONS

Lubberts Erik: "The role of IL-17 and family members in the pathogenesis of arthritis", Current Opinionin in Investigational Drugs, vol. 4, No. 5, pp. 572-577, (2003).

Tak, P.P.; et al., 73rd Annu Sci Meet Am Coll Rheumatol , Abstract No. 1922 , (Oct. 20, 2009).

Stoll, D.: et al., 18th Congr Eur Acad Dermatol Venereol (EADV), Abstract No. P1138 (Oct. 7-11, Berlin) 2009.

Durez, P.; et al., Annu Eur Congr Rheumatol (EULAR), Abstract No. LB0002 (Jun. 10-13, Copenhagen 2009).

Egan, P.J.; et al., Arthritis Rheum, 58(12): 3720, 2008.

U.S. Appl. No. 11/502,622, filed Aug. 11, 2006.

Dumont F.J., "IL-17 Cytokind/Receptor Families: Emerging Targets for the Modulation of Inflammatory Responses", Expert Opinion on Therapeutic Patents, vol. 13, No. 3, pp. 287-303, (2003).

Bhat, N. M. et al., Definition: Ig V kappa IIb [human, mRNA Partial, 327 nt]., Database DDB/EMBL/GenBank [online], Accession No. S66 101, Nov. 29, 1993 uploaded, Apr. 8, 2010 http://www.ncbi.nlm.nih.govsviewer/viewer.fcgi ?430845:OLDID:553059.

The abstract Journal of the 45$^{th}$ Japan Digestive Disease Week, Sep. 20, 2003, p. A678.

The abstract Journal of the 45$^{th}$ Japan Digestive Week, Sep. 20, 2003, p. A675.

The abstract Journal of the 14$^{th}$ Japanese Society for Host Defense Research, Jul. 31, 2003, p. 33.

Kasai, N. et al., The Introductory immunology, Kodansha, 1989, the first edition, p. 41-42.

Japanese office action (translation) dated Apr. 20, 2010 (for corresponding JP Patent application No. 524286/2007).

Uk Search Report, dated Nov. 29, 2004, for corresponding case UK 0417487.6, filed Aug. 5, 2004.

Translation of The abstract Journal of the 45$^{th}$ Japan Digestive Week, Sep. 20, 2003, p. A678 (denoted "English Translation of Reference 6").

Translation of The abstract Journal of the 45$^{th}$ Japan Digestive Week, Sep. 20 2003, p. A675 (denoted "English Translation of Reference 7").

Translation of The abstract Journal of the 14$^{th}$ Japan Society for Host l efense Research, Jul. 31, 2003, p. 33 (denoted "English Translation of Reference 8").

Translation of Kasai, N. et al., The Introductory immunology, Kodansha, 1989, the first edition, p. 41-42 (denoted "English Translation of Reference 9").

* cited by examiner

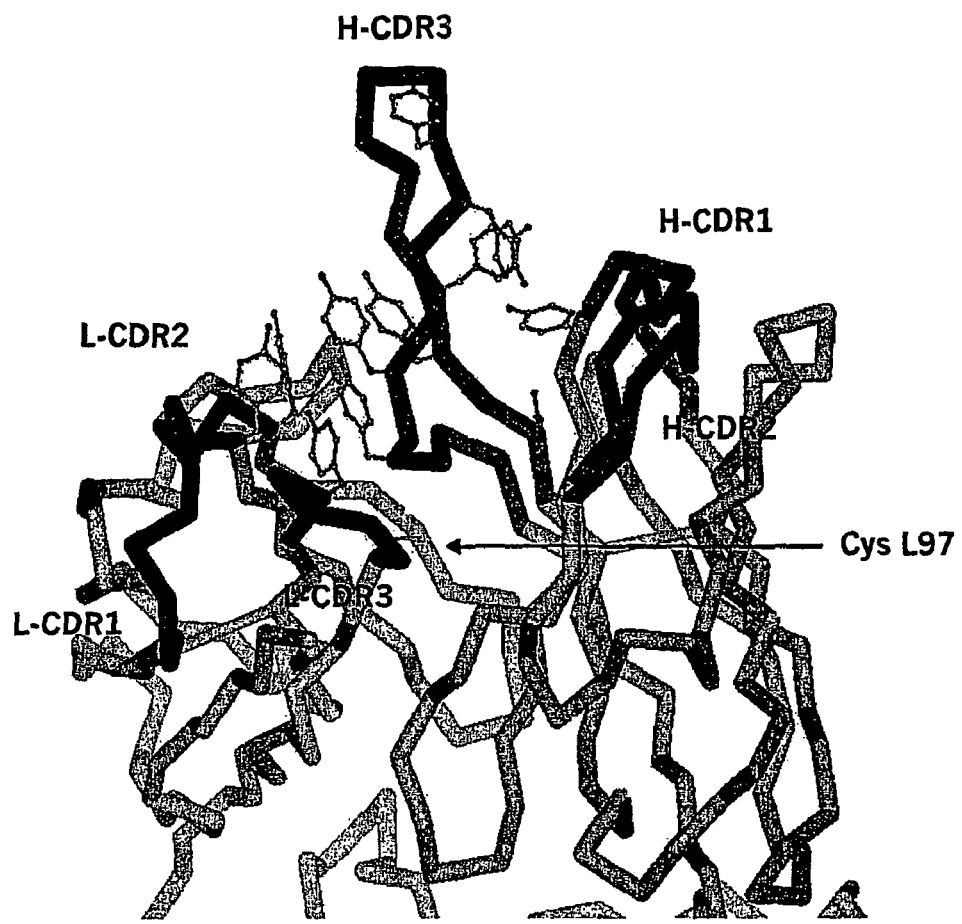

Figure 1. X-ray structure of AIN457 Fab

Close-up view of the variable domains of the AIN457 Fab (Cα trace) with complementarity-determining regions highlighted. All tyrosine side-chains contributed by the CDR loops are shown, to illustrate the fact that the antigen-combining site of AIN457 is exceptionnally rich in tyrosine residues. The side-chain of Cys L97, at the $V_L$-$V_H$ interface, is also shown (arrow).

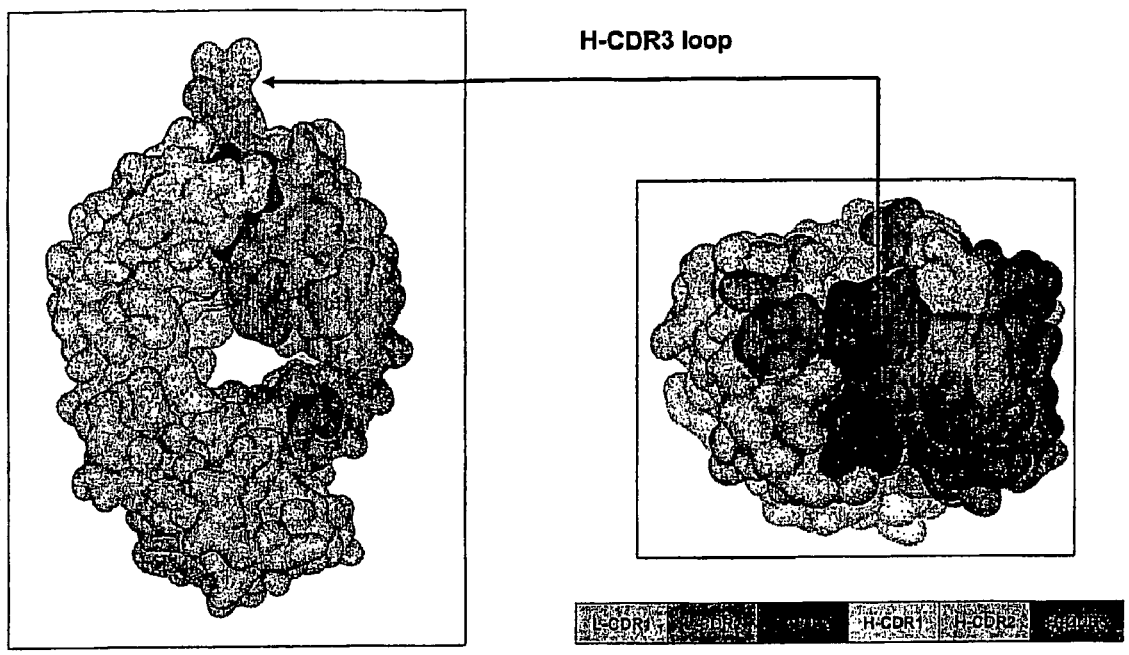
Figure 2. X-ray structure of AIN457 Fab, overall view
Van der Waals surface representation of AIN457 Fab. The light and heavy chain are coloured light and dark grey, respectively. CDR loops are highlighted in different colours. Note the presence of the very loop H-CDR3 loop protruding out of the antigen-combining site of the antibody.

SEQUENCE LISTING

<160> NUMBER OF SEQ ID NOS: 28

<210> SEQ ID NO 1
<211> LENGTH: 5
<212> TYPE: PRT

```
<213> ORGANISM: artificial
<220> FEATURE:
<223> OTHER INFORMATION: CDR1 = hypervariable region 1 of heavy chain of
      AIN457

<400> SEQUENCE: 1

Asn Tyr Trp Met Asn
1               5

<210> SEQ ID NO 2
<211> LENGTH: 17
<212> TYPE: PRT
<213> ORGANISM: ARTIFICIAL
<220> FEATURE:
<223> OTHER INFORMATION: CDR2 = hypervariable region 2 of heavy chain of
      AIN457

<400> SEQUENCE: 2

Ala Ile Asn Gln Asp Gly Ser Glu Lys Tyr Tyr Val Gly Ser Val Lys
1               5                   10                  15

Gly

<210> SEQ ID NO 3
<211> LENGTH: 18
<212> TYPE: PRT
<213> ORGANISM: ARTIFICIAL
<220> FEATURE:
<223> OTHER INFORMATION: CDR3 = hypervariable region 3 of heavy chain of
      AIN457

<400> SEQUENCE: 3

Asp Tyr Tyr Asp Ile Leu Thr Asp Tyr Tyr Ile His Tyr Trp Tyr Phe
1               5                   10                  15

Asp Leu

<210> SEQ ID NO 4
<211> LENGTH: 12
<212> TYPE: PRT
<213> ORGANISM: ARTIFICIAL
<220> FEATURE:
<223> OTHER INFORMATION: CDR1' = hypervariable region 1 of light chain
      of AIN457

<400> SEQUENCE: 4

Arg Ala Ser Gln Ser Val Ser Ser Ser Tyr Leu Ala
1               5                   10

<210> SEQ ID NO 5
<211> LENGTH: 7
<212> TYPE: PRT
<213> ORGANISM: ARTIFICIAL
<220> FEATURE:
<223> OTHER INFORMATION: CDR2' = hypervariable region 2 of light chain
      AIN457

<400> SEQUENCE: 5

Gly Ala Ser Ser Arg Ala Thr
1               5

<210> SEQ ID NO 6
<211> LENGTH: 9
<212> TYPE: PRT
<213> ORGANISM: ARTIFICIAL
<220> FEATURE:
<223> OTHER INFORMATION: CDR3' = hypervariable region 3 of light chain
      AIN457
```

-continued

<400> SEQUENCE: 6

Gln Gln Tyr Gly Ser Ser Pro Cys Thr
1               5

<210> SEQ ID NO 7
<211> LENGTH: 381
<212> TYPE: DNA
<213> ORGANISM: HOMO SAPIENS
<220> FEATURE:
<221> NAME/KEY: CDS
<222> LOCATION: (1)..(381)

<400> SEQUENCE: 7

```
gag gtg cag ttg gtg gag tct ggg gga ggc ttg gtc cag cct ggg ggg      48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agt aac tat      96
Ser Leu Arg Leu Ser Cys Ala Ala Ser Gly Phe Thr Phe Ser Asn Tyr
            20                  25                  30 tgg atg aac tgg gtc cgc cag gct cca ggg aaa ggg ctg gag tgg gtg     144
Trp Met Asn Trp Val Arg Gln Ala Pro Gly Lys Gly Leu Glu Trp Val
        35                  40                  45 gcc gcc ata aac caa gat gga agt gag aaa tac tat gtg ggc tct gtg     192
Ala Ala Ile Asn Gln Asp Gly Ser Glu Lys Tyr Tyr Val Gly Ser Val
    50                  55                  60 aag ggc cga ttc acc atc tcc aga gac aac gcc aag aac tca ctg tat     240
Lys Gly Arg Phe Thr Ile Ser Arg Asp Asn Ala Lys Asn Ser Leu Tyr
65                  70                  75                  80 ctg caa atg aac agc ctg aga gtc gag gac acg gct gtg tat tac tgt     288
Leu Gln Met Asn Ser Leu Arg Val Glu Asp Thr Ala Val Tyr Tyr Cys
                85                  90                  95 gtg agg gac tat tac gat att ttg acc gat tat tac atc cac tat tgg     336
Val Arg Asp Tyr Tyr Asp Ile Leu Thr Asp Tyr Tyr Ile His Tyr Trp
            100                 105                 110 tac ttc gat ctc tgg ggc cgt ggc acc ctg gtc act gtc tcc tca         381
Tyr Phe Asp Leu Trp Gly Arg Gly Thr Leu Val Thr Val Ser Ser
        115                 120                 125
```

<210> SEQ ID NO 8
<211> LENGTH: 127
<212> TYPE: PRT
<213> ORGANISM: HOMO SAPIENS

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

```
<210> SEQ ID NO 9
<211> LENGTH: 327
<212> TYPE: DNA
<213> ORGANISM: HOMO SAPIENS
<220> FEATURE:
<221> NAME/KEY: CDS
<222> LOCATION: (1)..(327)

<400> SEQUENCE: 9 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
                20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
            35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat ggt agc tca ccg     288
Pro Glu Asp Phe Ala Val Tyr Tyr Cys Gln Gln Tyr Gly Ser Ser Pro
                85                  90                  95 tgc acc ttc ggc caa ggg aca cga ctg gag att aaa cga                 327
Cys Thr Phe Gly Gln Gly Thr Arg Leu Glu Ile Lys Arg
                100                 105

<210> SEQ ID NO 10
<211> LENGTH: 109
<212> TYPE: PRT
<213> ORGANISM: HOMO SAPIENS

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Thr Phe Gly Gln Gly Thr Arg Leu Glu Ile Lys Arg
                100                 105

<210> SEQ ID NO 11
<211> LENGTH: 10
<212> TYPE: PRT
<213> ORGANISM: artificial
<220> FEATURE:
<223> OTHER INFORMATION: CDR1-x = hypervariable domain x of heavy chain
      of AIN457

<400> SEQUENCE: 11
```

```
Gly Phe Thr Phe Ser Asn Tyr Trp Met Asn
1               5                   10

<210> SEQ ID NO 12
<211> LENGTH: 11
<212> TYPE: PRT
<213> ORGANISM: artificial
<220> FEATURE:
<223> OTHER INFORMATION: CDR2-x = hypervariable domain of heavy chain x
      of AIN457

<400> SEQUENCE: 12

Ala Ile Asn Gln Asp Gly Ser Glu Lys Tyr Tyr
1               5                   10

<210> SEQ ID NO 13
<211> LENGTH: 23
<212> TYPE: PRT
<213> ORGANISM: ARTIFICIAL
<220> FEATURE:
<223> OTHER INFORMATION: CDR3-x = hypervariable domain x of heavy chain
      AIN457

<400> SEQUENCE: 13

Cys Val Arg Asp Tyr Tyr Asp Ile Leu Thr Asp Tyr Tyr Ile His Tyr
1               5                   10                  15

Trp Tyr Phe Asp Leu Trp Gly
            20

<210> SEQ ID NO 14
<211> LENGTH: 20
<212> TYPE: DNA
<213> ORGANISM: ARTIFICIAL
<220> FEATURE:
<223> OTHER INFORMATION: Primer for cloning of heavy chain of AIN457

<400> SEQUENCE: 14
gactattacg atattttgac                                                 20

<210> SEQ ID NO 15
<211> LENGTH: 20
<212> TYPE: DNA
<213> ORGANISM: ARTIFICIAL
<220> FEATURE:
<223> OTHER INFORMATION: primer for cloning heavy chain of AIN457

<400> SEQUENCE: 15
gcctccacca agggcccatc                                                 20

<210> SEQ ID NO 16
<211> LENGTH: 20
<212> TYPE: DNA
<213> ORGANISM: artificial
<220> FEATURE:
<223> OTHER INFORMATION: primer for cloning heavy chain of AIN457

<400> SEQUENCE: 16
tggttcccgg gtagccagaa                                                 20

<210> SEQ ID NO 17
<211> LENGTH: 20
<212> TYPE: DNA
<213> ORGANISM: ARTIFICIAL
<220> FEATURE:
<223> OTHER INFORMATION: primer for cloning of heavy chain of AIN457
```

```
<400> SEQUENCE: 17
ccacctgttc tctcaactcg                                           20

<210> SEQ ID NO 18
<211> LENGTH: 24
<212> TYPE: DNA
<213> ORGANISM: ARTIFICIAL
<220> FEATURE:
<223> OTHER INFORMATION: PCR of AIN457 heavy chain

<400> SEQUENCE: 18
accatggaat tggggctgag ctgg                                      24

<210> SEQ ID NO 19
<211> LENGTH: 26
<212> TYPE: DNA
<213> ORGANISM: ARTIFICIAL
<220> FEATURE:
<223> OTHER INFORMATION: PCR of AIN457 heavy chain

<400> SEQUENCE: 19
gagtgtgtac gggtggcacg ggtatt                                    26

<210> SEQ ID NO 20
<211> LENGTH: 21
<212> TYPE: DNA
<213> ORGANISM: ARTIFICIAL
<220> FEATURE:
<223> OTHER INFORMATION: PCR of AIN457 heavy chain

<400> SEQUENCE: 20
gaggtgcagt tggtggagtc t                                         21

<210> SEQ ID NO 21
<211> LENGTH: 24
<212> TYPE: DNA
<213> ORGANISM: ARTIFICIAL
<220> FEATURE:
<223> OTHER INFORMATION: PCR of AIN457 light chain

<400> SEQUENCE: 21
accatggaaa ccccagcgga gctt                                      24

<210> SEQ ID NO 22
<211> LENGTH: 22
<212> TYPE: DNA
<213> ORGANISM: ARTIFICIAL
<220> FEATURE:
<223> OTHER INFORMATION: PCR of AIN457 light chain

<400> SEQUENCE: 22
gaagttgtcc cctctcacaa tc                                        22

<210> SEQ ID NO 23
<211> LENGTH: 21
<212> TYPE: DNA
<213> ORGANISM: artificial
<220> FEATURE:
<223> OTHER INFORMATION: PCR of AIN457 light chain

<400> SEQUENCE: 23
gaaattgtgt tgacgcagtc t                                         21

<210> SEQ ID NO 24
<211> LENGTH: 711
```

<212> TYPE: DNA
<213> ORGANISM: HOMO SAPIENS
<220> FEATURE:
<221> NAME/KEY: CDS
<222> LOCATION: (1)..(708)

<400> SEQUENCE: 24

```
acc atg gaa acc cca gcg gag ctt ctc ttc ctc ctg cta ctc tgg ctc     48
Thr Met Glu Thr Pro Ala Glu Leu Leu Phe Leu Leu Leu Leu Trp Leu
1               5                   10                  15 cca gat acc acc gga gaa att gtg ttg acg cag tct cca ggc acc ctg     96
Pro Asp Thr Thr Gly Glu Ile Val Leu Thr Gln Ser Pro Gly Thr Leu
            20                  25                  30 tct ttg tct cca ggg gaa aga gcc acc ctc tcc tgc agg gcc agt cag    144
Ser Leu Ser Pro Gly Glu Arg Ala Thr Leu Ser Cys Arg Ala Ser Gln
        35                  40                  45 agt gtt agc agc agc tac tta gcc tgg tac cag cag aaa cct ggc cag    192
Ser Val Ser Ser Ser Tyr Leu Ala Trp Tyr Gln Gln Lys Pro Gly Gln
    50                  55                  60 gct ccc agg ctc ctc atc tat ggt gca tcc agc agg gcc act ggc atc    240
Ala Pro Arg Leu Leu Ile Tyr Gly Ala Ser Ser Arg Ala Thr Gly Ile
65                  70                  75                  80 cca gac agg ttc agt ggc agt ggg tct ggg aca gac ttc act ctc acc    288
Pro Asp Arg Phe Ser Gly Ser Gly Ser Gly Thr Asp Phe Thr Leu Thr
                85                  90                  95 atc agc aga ctg gag cct gaa gat ttt gca gtg tat tac tgt cag cag    336
Ile Ser Arg Leu Glu Pro Glu Asp Phe Ala Val Tyr Tyr Cys Gln Gln
            100                 105                 110 tat ggt agc tca ccg tgc acc ttc ggc caa ggg aca cga ctg gag att    384
Tyr Gly Ser Ser Pro Cys Thr Phe Gly Gln Gly Thr Arg Leu Glu Ile
        115                 120                 125 aaa cga act gtg gct gca cca tct gtc ttc atc ttc ccg cca tct gat    432
Lys Arg Thr Val Ala Ala Pro Ser Val Phe Ile Phe Pro Pro Ser Asp
    130                 135                 140 gag cag ttg aaa tct gga act gcc tct gtt gtg tgc ctg ctg aat aac    480
Glu Gln Leu Lys Ser Gly Thr Ala Ser Val Val Cys Leu Leu Asn Asn
145                 150                 155                 160 ttc tat ccc aga gag gcc aaa gta cag tgg aag gtg gat aac gcc ctc    528
Phe Tyr Pro Arg Glu Ala Lys Val Gln Trp Lys Val Asp Asn Ala Leu
                165                 170                 175 caa tcg ggt aac tcc cag gag agt gtc aca gag cag gac agc aag gac    576
Gln Ser Gly Asn Ser Gln Glu Ser Val Thr Glu Gln Asp Ser Lys Asp
            180                 185                 190 agc acc tac agc ctc agc agc acc ctg acg ctg agc aaa gca gac tac    624
Ser Thr Tyr Ser Leu Ser Ser Thr Leu Thr Leu Ser Lys Ala Asp Tyr
        195                 200                 205 gag aaa cac aaa gtc tac gcc tgc gaa gtc acc cat cag ggc ctg agc    672
Glu Lys His Lys Val Tyr Ala Cys Glu Val Thr His Gln Gly Leu Ser
    210                 215                 220 tcg ccc gtc aca aag agc ttc aac agg gga gag tgt tag               711
Ser Pro Val Thr Lys Ser Phe Asn Arg Gly Glu Cys
225                 230                 235
```

<210> SEQ ID NO 25
<211> LENGTH: 236
<212> TYPE: PRT
<213> ORGANISM: HOMO SAPIENS

<400> SEQUENCE: 25

```
Thr Met Glu Thr Pro Ala Glu Leu Leu Phe Leu Leu Leu Leu Trp Leu
1               5                   10                  15
```

-continued

```
Pro Asp Thr Thr Gly Glu Ile Val Leu Thr Gln Ser Pro Gly Thr Leu
         20                  25                  30
Ser Leu Ser Pro Gly Glu Arg Ala Thr Leu Ser Cys Arg Ala Ser Gln
     35                  40                  45
Ser Val Ser Ser Ser Tyr Leu Ala Trp Tyr Gln Gln Lys Pro Gly Gln
 50                  55                  60
Ala Pro Arg Leu Leu Ile Tyr Gly Ala Ser Ser Arg Ala Thr Gly Ile
65                  70                  75                  80
Pro Asp Arg Phe Ser Gly Ser Gly Ser Gly Thr Asp Phe Thr Leu Thr
                 85                  90                  95
Ile Ser Arg Leu Glu Pro Glu Asp Phe Ala Val Tyr Tyr Cys Gln Gln
            100                 105                 110
Tyr Gly Ser Ser Pro Cys Thr Phe Gly Gln Gly Thr Arg Leu Glu Ile
        115                 120                 125
Lys Arg Thr Val Ala Ala Pro Ser Val Phe Ile Phe Pro Pro Ser Asp
    130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235
```

<210> SEQ ID NO 26
<211> LENGTH: 711
<212> TYPE: DNA
<213> ORGANISM: HOMO SAPIENS

<400> SEQUENCE: 26

```
tggtaccttt ggggtcgcct cgaagagaag gaggacgatg agaccgaggg tctatggtgg    60
cctctttaac acaactgcgt cagaggtccg tgggacagaa acagaggtcc cctttctcgg   120
tgggagagga cgtcccggtc agtctcacaa tcgtcgtcga tgaatcggac catggtcgtc   180
tttggaccgg tccgagggtc cgaggagtag ataccacgta ggtcgtcccg gtgaccgtag   240
ggtctgtcca agtcaccgtc acccagaccc tgtctgaagt gagagtggta gtcgtctgac   300
ctcggacttc taaaacgtca cataatgaca gtcgtcatac catcgagtgg agcgtggaag   360
ccggttccct gtgctgacct ctaatttgct tgacaccgac gtggtagaca gaagtagaag   420
ggcggtagac tactcgtcaa ctttagacct tgacggagac aacacacgga cgacttattg   480
aagatagggt ctctccggtt tcatgtcacc ttccacctat gcgggaggt tagcccattg    540
agggtcctct cacagtgtct cgtcctgtcg ttcctgtcgt ggatgtcgga gtcgtcgtgg   600
gactgcgact cgtttcgtct gatgctcttt gtgtttcaga tgcggacgct tcagtgggta   660
gtcccggact cgagcgggca gtgtttctcg aagttgtccc ctctcacaat c             711
```

<210> SEQ ID NO 27
<211> LENGTH: 783
<212> TYPE: DNA
<213> ORGANISM: HOMO SAPIENS

```
<220> FEATURE:
<221> NAME/KEY: CDS
<222> LOCATION: (1)..(780)

<400> SEQUENCE: 27 acc atg gaa ttg ggg ctg agc tgg gtt ttc ctt gtt gct att tta gaa      48
Thr Met Glu Leu Gly Leu Ser Trp Val Phe Leu Val Ala Ile Leu Glu
 1               5                  10                  15 ggt gtc cac tgt gag gtg cag ttg gtg gag tct ggg gga ggc ttg gtc      96
Gly Val His Cys Glu Val Gln Leu Val Glu Ser Gly Gly Gly Leu Val
             20                  25                  30 cag cct ggg ggg tcc ctg aga ctc tcc tgt gca gcc tct gga ttc acc     144
Gln Pro Gly Gly Ser Leu Arg Leu Ser Cys Ala Ala Ser Gly Phe Thr
         35                  40                  45 ttt agt aac tat tgg atg aac tgg gtc cgc cag gct cca ggg aaa ggg     192
Phe Ser Asn Tyr Trp Met Asn Trp Val Arg Gln Ala Pro Gly Lys Gly
     50                  55                  60 ctg gag tgg gtg gcc gcc ata aac caa gat gga agt gag aaa tac tat     240
Leu Glu Trp Val Ala Ala Ile Asn Gln Asp Gly Ser Glu Lys Tyr Tyr
 65                  70                  75                  80 gtg ggc tct gtg aag ggc cga ttc acc atc tcc aga gac aac gcc aag     288
Val Gly Ser Val Lys Gly Arg Phe Thr Ile Ser Arg Asp Asn Ala Lys
                 85                  90                  95 aac tca ctg tat ctg caa atg aac agc ctg aga gtc gag gac acg gct     336
Asn Ser Leu Tyr Leu Gln Met Asn Ser Leu Arg Val Glu Asp Thr Ala
            100                 105                 110 gtg tat tac tgt gtg agg gac tat tac gat att ttg acc gat tat tac     384
Val Tyr Tyr Cys Val Arg Asp Tyr Tyr Asp Ile Leu Thr Asp Tyr Tyr
        115                 120                 125 atc cac tat tgg tac ttc gat ctc tgg ggc cgt ggc acc ctg gtc act     432
Ile His Tyr Trp Tyr Phe Asp Leu Trp Gly Arg Gly Thr Leu Val Thr
    130                 135                 140 gtc tcc tca gcc tcc acc aag ggc cca tcg gtc ttc ccc ctg gca ccc     480
Val Ser Ser Ala Ser Thr Lys Gly Pro Ser Val Phe Pro Leu Ala Pro
145                 150                 155                 160 tcc tcc aag agc acc tct ggg ggc aca gcg gcc ctg ggc tgc ctg gtc     528
Ser Ser Lys Ser Thr Ser Gly Gly Thr Ala Ala Leu Gly Cys Leu Val
                165                 170                 175 aag gac tac ttc ccc gaa ccg gtg acg gtg tcg tgg aac tca ggc gcc     576
Lys Asp Tyr Phe Pro Glu Pro Val Thr Val Ser Trp Asn Ser Gly Ala
            180                 185                 190 ctg acc agc ggc gtg cac acc ttc ccg gct gtc cta cag tcc tca gga     624
Leu Thr Ser Gly Val His Thr Phe Pro Ala Val Leu Gln Ser Ser Gly
        195                 200                 205 ctc tac tcc ctc agc agc gtg gtg acc gtg ccc tcc agc agc ttg ggc     672
Leu Tyr Ser Leu Ser Ser Val Val Thr Val Pro Ser Ser Ser Leu Gly
    210                 215                 220 acc cag acc tac atc tgc aac gtg aat cac aag ccc agc aac acc aag     720
Thr Gln Thr Tyr Ile Cys Asn Val Asn His Lys Pro Ser Asn Thr Lys
225                 230                 235                 240 gtg gac aag aga gtt gag ccc aaa tct tgt gac aaa act cac aca tgc     768
Val Asp Lys Arg Val Glu Pro Lys Ser Cys Asp Lys Thr His Thr Cys
                245                 250                 255 cca ccg tgc cca taa                                                  783
Pro Pro Cys Pro
            260

<210> SEQ ID NO 28
<211> LENGTH: 260
<212> TYPE: PRT
<213> ORGANISM: HOMO SAPIENS
```

```
<400> SEQUENCE: 28

Thr Met Glu Leu Gly Leu Ser Trp Val Phe Leu Val Ala Ile Leu Glu
1               5                   10                  15

Gly Val His Cys Glu Val Gln Leu Val Glu Ser Gly Gly Gly Leu Val
                20                  25                  30

Gln Pro Gly Gly Ser Leu Arg Leu Ser Cys Ala Ala Ser Gly Phe Thr
            35                  40                  45

Phe Ser Asn Tyr Trp Met Asn Trp Val Arg Gln Ala Pro Gly Lys Gly
        50                  55                  60

Leu Glu Trp Val Ala Ala Ile Asn Gln Asp Gly Ser Glu Lys Tyr Tyr
65                  70                  75                  80

Val Gly Ser Val Lys Gly Arg Phe Thr Ile Ser Arg Asp Asn Ala Lys
                85                  90                  95

Asn Ser Leu Tyr Leu Gln Met Asn Ser Leu Arg Val Glu Asp Thr Ala
                100                 105                 110

Val Tyr Tyr Cys Val Arg Asp Tyr Tyr Asp Ile Leu Thr Asp Tyr Tyr
            115                 120                 125

Ile His Tyr Trp Tyr Phe Asp Leu Trp Gly Arg Gly Thr Leu Val Thr
        130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Arg Val Glu Pro Lys Ser Cys Asp Lys Thr His Thr Cys
                245                 250                 255

Pro Pro Cys Pro
            260
```

IL-17 ANTAGONISTIC ANTIBODIES

This application is a National Phase entry of PCT/EP/2005/008470, filed Aug. 4, 2005, which claims priority to European Patent Application EP0417487.6, filed Aug. 5, 2004.

FIELD OF THE DISCLOSURE

This invention relates to an IL-17 binding molecule, in particular an antibody to human IL-17, more preferably a human antibody to human IL-17 (also named IL-17A) and to the use of such antibodies in the treatment of IL-17 mediated diseases and disorders.

BACKGROUND OF THE DISCLOSURE

IL-17, a T-cell derived cytokine present e.g. in rheumatoid arthritis (RA), acts as a pro-inflammatory cytokine, particularly in conjunction with IL-1 and TNF-α (Chabaud M & Miossec P (1999) Arthritis Rheum 42, 963-970; Awane M et al (1999) J. Immunol 162, 5337-5344). IL-17 induces MMP production and downregulates TIMP (Jovanovic D V et al (2001) J. Rheumatol. 28, 712-718), and blockage of IL-1 and IL-17 has a synergistic effect on inflammation and bone destruction in vivo (Chabaud M & Miossec (2001) Arthritis Rheum 44, 1293-1303). Inappropriate or excessive production of IL-17 is associated with the pathology of various diseases and disorders, such as rheumatoid arthritis (Witowski et al., 2004 Cell Mol Life Sci 61:567-579), osteoarthritis, loosening of bone implants, acute transplant rejection (Antonysamy et al., 1999, J Immunol 162, 577-584; van Kooten et al., 1998, J Am Soc Nephrol 9, 1526-1534), septicemia, septic or endotoxic shock, allergies, asthma (Molet et al., 2001, J Allergy Clin Immunol 108, 430-438), bone loss, psoriasis (Teunissen et al., 1998, J Invest Dernatol 111, 645-649), ischemia, systemic sclerosis (Kurasawa et al., 2000, Arthritis Rheum 43, 2455-2463), stroke, and other inflammatory disorders. Antibodies to IL-17 have been proposed for use in the treatment of IL-17 mediated diseases and disorders; see for instance, WO 95/18826 and the discussion in the introduction thereof.

SUMMARY OF THE DISCLOSURE

We have now prepared improved antibodies to human IL-17 suitable for use in the treatment of IL-17 mediated diseases and disorders.

Accordingly the invention provides an IL-17 binding molecule which comprises an antigen binding site comprising at least one immunoglobulin heavy chain variable domain ($V_H$) which comprises in sequence hypervariable regions CDR1, CDR2 and CDR3, said CDR1 having the amino acid sequence SEQ ID NO: 1 (N-Y-W-M-N), said CDR2 having the amino acid sequence SEQ ID NO: 2 (A-I-N-Q-D-G-S-E-K-Y-Y-V-G-S-V-K-G), and said CDR3 having the amino acid sequence SEQ ID NO: 3 (D-Y-Y-D-I-L-T-D-Y-Y-I-H-Y-W-Y-F-D-L); or direct CDR equivalents thereof.

Accordingly the invention also provides an IL-17 binding molecule comprising at least one immunoglobulin light chain variable domain ($V_L$) which comprises in sequence hypervariable regions CDR1', CDR2' and CDR3', said CDR1' having the amino acid sequence SEQ ID NO: 4 (R-A-S-Q-S-V-S-S-S-Y-L-A), said CDR2' having the amino acid sequence SEQ ID NO: 5 (G-A-S-S-R-A-T) and said CDR3' having the amino acid sequence SEQ ID NO: 6 (Q-Q-Y-G-S-S-P-C-T) or direct CDR' equivalents thereof.

In another embodiment of the invention, the invention provides an IL-17 binding molecule which comprises an antigen binding site comprising at least one immunoglobulin heavy chain variable domain ($V_H$) which comprises in sequence hypervariable regions CDR1-x, CDR2-x and CDR3-x, said CDR1-x having the amino acid sequence SEQ ID NO: 11 (G-F-T-F-S-N-Y-W-M-N), said CDR2-x having the amino acid sequence SEQ ID NO: 12 (A-I-N-Q-D-G-S-E-K-Y-Y), and said CDR3-x having the amino acid sequence SEQ ID NO: 13 (C-V-R-D-Y-Y-D-I-L-T-D-Y-Y-I-H-Y-W-Y-F-D-L-W-G); or direct CDR-x equivalents thereof.

Furthermore, the invention also provides an IL-17 binding molecule comprising both heavy ($V_H$) and light chain ($V_L$) variable domains; said IL-17 binding molecule comprises at least one antigen binding site comprising:

a) an immunoglobulin heavy chain variable domain ($V_H$) which comprises in sequence hypervariable regions CDR1, CDR2 and CDR3, said CDR1 having the amino acid sequence SEQ ID NO: 1, said CDR2 having the amino acid sequence SEQ ID NO:2, and said CDR3 having the amino acid sequence SEQ ID NO:3 or direct CDR equivalents thereof; and b) an immunoglobulin light chain variable domain ($V_L$) which comprises in sequence hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6 or direct CDR' equivalents thereof.

Moreover, the invention also provides an IL-17 binding molecule comprising both heavy ($V_H$) and light chain ($V_L$) variable domains; said IL-17 binding molecule comprises at least one antigen binding site comprising:

a) an immunoglobulin heavy chain variable domain ($V_H$) which comprises in sequence hypervariable regions CDR1-x, CDR2-x and CDR3-x, said CDR1-x having the amino acid sequence SEQ ID NO:11, said CDR2-x having the amino acid sequence SEQ ID NO:12, and said CDR3-x having the amino acid sequence SEQ ID NO:13 or direct CDR-x equivalents thereof; and b) an immunoglobulin light chain variable domain ($V_L$) which comprises in sequence hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6 or direct CDR' equivalents thereof.

Unless otherwise indicated, any polypeptide chain is herein described as having an amino acid sequence starting at the N-terminal extremity and ending at the C-terminal extremity. When the antigen binding site comprises both the $V_H$ and $V_L$ domains, these may be located on the same polypeptide molecule or, preferably, each domain may be on a different chain, the $V_H$ domain being part of an immunoglobulin heavy chain or fragment thereof and the $V_L$ being part of an immunoglobulin light chain or fragment thereof.

BRIEF DESCRIPTION OF THE DRAWINGS

FIG. 1 shows a close-up view of the variable domains of the AIN457 Fab (Cα trace) with complementarity-determining regions highlighted. All tyrosine side-chains contributed by the CDR loops are shown, to illustrate the fact that the antigen-combining site of AIN457 is exceptionally rich in tyrosine residues. The side-chain of Cys L97, at the $V_L$-$V_H$ interface, is also shown (arrow).

FIG. 2 Shows a Van der Waals surface representation of AIN457 Fab. The light and heavy chain are coloured light and dark grey, respectively. CDR loops are highlighted in different colours. Note the presence of the very loop H-CDR3 loop protruding out of the antigen-combining site of the antibody.

DETAILED DESCRIPTION OF THE DISCLOSURE

By "IL-17 binding molecule" is meant any molecule capable of binding to the IL-17 antigen either alone or associated with other molecules. The binding reaction may be shown by standard methods (qualitative assays) including, for example, a binding assay, competition assay or a bioassay for determining the inhibition of IL-17 binding to its receptor or any kind of binding assays, with reference to a negative control test in which an antibody of unrelated specificity but of the same isotype, e.g. an anti-CD25 antibody, is used (see also Example 1).

Examples of antigen binding molecules include antibodies as produced by B-cells or hybridomas and chimeric, CDR-grafted or human antibodies or any fragment thereof, e.g. F(ab')$_2$ and Fab fragments, as well as single chain or single domain antibodies.

A single chain antibody consists of the variable domains of the heavy and light chains of an antibody covalently bound by a peptide linker usually consisting of from 10 to 30 amino acids, preferably from 15 to 25 amino acids. Therefore, such a structure does not include the constant part of the heavy and light chains and it is believed that the small peptide spacer should be less antigenic than a whole constant part. By "chimeric antibody" is meant an antibody in which the constant regions of heavy or light chains or both are of human origin while the variable domains of both heavy and light chains are of non-human (e.g. murine) origin or of human origin but derived from a different human antibody. By "CDR-grafted antibody" is meant an antibody in which the hypervariable regions (CDRs) are derived from a donor antibody, such as a non-human (e.g. murine) antibody or a different human antibody, while all or substantially all the other parts of the immunoglobulin e.g. the constant regions and the highly conserved parts of the variable domains, i.e. the framework regions, are derived from an acceptor antibody, e.g. an antibody of human origin. A CDR-grafted antibody may however contain a few amino acids of the donor sequence in the framework regions, for instance in the parts of the framework regions adjacent to the hypervariable regions. By "human antibody" is meant an antibody in which the constant and variable regions of both the heavy and light chains are all of human origin, or substantially identical to sequences of human origin, not necessarily from the same antibody and includes antibodies produced by mice in which the murine immunoglobulin variable and constant part genes have been replaced by their human counterparts, e.g. as described in general terms in EP 0546073 B1, U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770,429, EP 0438474 B1 and EP 0463151 B1.

Particularly preferred IL-17 binding molecules of the invention are human antibodies, especially the AIN457 antibody as hereinafter described in Examples 1 and 2.

Thus in preferred chimeric antibodies the variable domains of both heavy and light chains are of human origin, for instance those of the AIN457 antibody which are shown in SEQ ID NO: 10 (=variable domain of light chain, i.e. amino acid 1 to 109 of SEQ ID NO: 10) and SEQ ID NO: 8 (=variable domain of heavy chain, i.e. amino acid 1 to 127 of SEQ ID NO: 8). The constant region domains preferably also comprise suitable human constant region domains, for instance as described in "Sequences of Proteins of Immunological Interest", Kabat E. A. et al, US Department of Health and Human Services, Public Health Service, National Institute of Health.

Hypervariable regions may be associated with any kind of framework regions, though preferably are of human origin. Suitable framework regions are described in Kabat E. A. et al, ibid. The preferred heavy chain framework is a human heavy chain framework, for instance that of the AIN457 antibody. It consists in sequence e.g. of FR1 (amino acid 1 to 30 of SEQ ID NO: 8), FR2 (amino acid 36 to 49 of SEQ ID NO: 8), FR3 (amino acid 67 to 98 of SEQ ID NO: 8) and FR4 (amino acid 117 to 127 of SEQ ID NO: 8) regions. Taking into consideration the determined hypervariable regions of AIN457 by X-ray analysis, another preferred heavy chain framework consists in sequence of FR1-x (amino acid 1 to 25 of SEQ ID NO: 8), FR2-x (amino acid 36 to 49 of SEQ ID NO: 8), FR3-x (amino acid 61 to 95 of SEQ ID NO: 8) and FR4 (amino acid 119 to 127 of SEQ ID NO: 8) regions. In a similar manner, the light chain framework consists, in sequence, of FR1' (amino acid 1 to 23 of SEQ ID NO: 10), FR2' (amino acid 36 to 50 of SEQ ID NO: 10), FR3' (amino acid 58 to 89 of SEQ ID NO: 10) and FR4' (amino acid 99 to 109 of SEQ ID NO: 10) regions.

Accordingly, the invention also provides an IL-17 binding molecule which comprises at least one antigen binding site comprising either a first domain having an amino acid sequence substantially identical to that shown in SEQ ID NO: 8 starting with the amino acid at position 1 and ending with the amino acid at position 127 or a first domain as described above and a second domain having an amino acid sequence substantially identical to that shown in SEQ ID NO: 10, starting with the amino acid at position 1 and ending with the amino acid at position 109.

Monoclonal antibodies raised against a protein naturally found in all humans are typically developed in a non-human system e.g. in mice, and as such are typically non-human proteins. As a direct consequence of this, a xenogenic antibody as produced by a hybridoma, when administered to humans, elicits an undesirable immune response which is predominantly mediated by the constant part of the xenogenic immunoglobulin. This clearly limits the use of such antibodies as they cannot be administered over a prolonged period of time. Therefore it is particularly preferred to use single chain, single domain, chimeric, CDR-grafted, or especially human antibodies which are not likely to elicit a substantial allogenic response when administered to humans.

In view of the foregoing, a more preferred IL-17 binding molecule of the invention is selected from a human anti IL-17 antibody which comprises at least a) an immunoglobulin heavy chain or fragment thereof which comprises (i) a variable domain comprising in sequence the hypervariable regions CDR1, CDR2 and CDR3 or direct CDR equivalents thereof and (ii) the constant part or fragment thereof of a human heavy chain; said CDR1 having the amino acid sequence SEQ ID NO: 1, said CDR2 having the amino acid sequence SEQ ID NO: 2, and said CDR3 having the amino acid sequence SEQ ID NO: 3; and b) an immunoglobulin light chain or fragment thereof which comprises (i) a variable domain comprising in sequence the hypervariable regions and optionally also the CDR1', CDR2', and CDR3' hypervariable regions or direct CDR' equivalents thereof and (ii) the constant part or fragment thereof of a human light chain, said CDR1' having the amino acid sequence SEQ ID NO: 4, said CDR2' having the amino acid sequence SEQ ID NO: 5, and said CDR3' having the amino acid sequence SEQ ID NO: 6.

Alternatively, an IL-17 binding molecule of the invention may be selected from a single chain binding molecule which comprises an antigen binding site comprising
a) a first domain comprising in sequence the hypervariable regions CDR1, CDR2 and CDR3 or direct CDR equivalents thereof, said CDR1 having the amino acid sequence SEQ ID NO: 1, said CDR2 having the amino acid sequence SEQ ID NO: 2, and said CDR3 having the amino acid sequence SEQ ID NO: 3; and
b) a second domain comprising the hypervariable regions CDR1', CDR2' and CDR3' or direct CDR' equivalents thereof, said CDR1' having the amino acid sequence SEQ ID NO: 4, said CDR2' having the amino acid sequence SEQ ID NO: 5, and said CDR3' having the amino acid sequence SEQ ID NO: 6; and
c) a peptide linker which is bound either to the N-terminal extremity of the first domain and to the C-terminal extremity of the second domain or to the C-terminal extremity of the first domain and to the N-terminal extremity of the second domain.

As it is well known, minor changes in an amino acid sequence such as deletion, addition or substitution of one, a few or even several amino acids may lead to an allelic form of the original protein which has substantially identical properties.

Thus, by the term "direct CDR equivalents thereof" are meant IL-17 binding molecules comprising in sequence the hypervariable regions $CDR1_i$, $CDR2_i$, and $CDR3_i$, (instead of CDR1, CDR2, and CDR3), wherein
  (i) the hypervariable region $CDR1_i$ differs by 3, preferably 2, more preferably 1 amino acid(s) from the hypervariable region CDR1 as shown in SEQ ID NO: 1; and
  (ii) the hypervariable region $CDR2_i$ differs by 3, preferably 2, more preferably 1 amino acid(s) from the hypervariable region CDR2 as shown in SEQ ID NO: 2; and
  (iii) the hypervariable region $CDR3_i$ differs by 3, preferably 2, more preferably 1 amino acid(s) from the hypervariable region CDR3 as shown in SEQ ID NO: 3; and
  (iv) such a molecule comprising in sequence the hypervariable regions $CDR1_i$, $CDR2_i$, and $CDR3_i$ is capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

Similarly, by the term "direct CDR-x equivalents thereof" are meant IL-17 binding molecules comprising in sequence the hypervariable regions CDR1-x, $CDR2_i$-x, and $CDR3_i$-x, (instead of CDR1-x, CDR2-x, and CDR3-x), wherein
  (v) the hypervariable region $CDR1_i$-x differs by 3, preferably 2, more preferably 1 amino acid(s) from the hypervariable region CDR1-x as shown in SEQ ID NO: 11; and
  (vi) the hypervariable region $CDR2_i$-x differs by 3, preferably 2, more preferably 1 amino acid(s) from the hypervariable region CDR2-x as shown in SEQ ID NO: 12; and
  (vii) the hypervariable region $CDR3_i$-x differs by 3, preferably 2, more preferably 1 amino acid(s) from the hypervariable region CDR3-x as shown in SEQ ID NO: 13; and
  (viii) such a molecule comprising in sequence the hypervariable regions $CDR1_i$-x, $CDR2_i$-x, and $CDR3_i$-x is capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

Similarly, by the term "direct CDR' equivalents thereof" is meant a domain comprising in sequence the hypervariable regions $CDR1'_i$, $CDR2'_i$, and $CDR3'_i$, wherein
  (i) the hypervariable region $CDR1'_i$ differs by 3, preferably 2, more preferably 1 amino acid(s) from the hypervariable region CDR1' as shown in SEQ ID NO: 4; and
  (ii) the hypervariable region $CDR2'_i$ differs by 3, preferably 2, more preferably 1 amino acid(s) from the hypervariable region CDR2' as shown in SEQ ID NO: 5; and
  (iii) the hypervariable region $CDR3'_i$ differs by 3, preferably 2, more preferably 1 amino acid(s) from the hypervariable region CDR3' as shown in SEQ ID NO: 6; and
  (iv) such a molecule comprising in sequence the hypervariable regions $CDR1'_i$, $CDR2'_i$, and $CDR3'_i$ is capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

Alternatively, an IL-17 binding molecule of the invention may be an IL-17 binding molecule which comprises at least one antigen binding site comprising at least one immunoglobulin heavy chain variable domain ($V_H$) which comprises in sequence
a) hypervariable regions CDR1 (SEQ ID NO: 1), CDR2 (SEQ ID NO: 2) and CDR3 (SEQ ID NO: 3); or
b) hypervariable regions $CDR1_i$, $CDR2_i$, $CDR3_i$, said hypervariable region CDR1 differs by 3, preferably 2, more preferably 1 amino acid(s) from the hypervariable region of CDR1 as shown in SEQ ID NO: 1, said hypervariable region $CDR2_i$ differs by 3, preferably 2, more preferably 1 amino acid(s) from the hypervariable region of CDR2 as shown in SEQ ID NO: 2; and said hypervariable region $CDR3_i$ differs by 3, preferably 2, more preferably 1 amino acid(s) from the hypervariable region of CDR3 as shown in SEQ ID NO: 3; and said binding IL-17 molecule comprising in sequence the hypervariable regions $CDR1_x$, $CDR2_x$, and $CDR3_x$ is capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

Similarly, an IL-17 binding molecule of the invention may be an IL-17 binding molecule which comprises at least one antigen binding site comprising at least one immunoglobulin heavy chain variable domain ($V_H$) which comprises in sequence
a) hypervariable regions CDR1-x (SEQ ID NO: 11), CDR2-x (SEQ ID NO: 12) and CDR3-x (SEQ ID NO: 13); or
b) hypervariable regions $CDR1_i$-x, $CDR2_i$-x, $CDR3_i$-x, said hypervariable region $CDR1_i$-x differs by 3, preferably 2, more preferably 1 amino acid(s) from the hypervariable region of CDR1-x as shown in SEQ ID NO: 11, said hypervariable region $CDR2_i$-x differs by 3, preferably 2, more preferably 1 amino acid(s) from the hypervariable region of CDR2-x as shown in SEQ ID NO: 12; and said hypervariable region $CDR3_i$-x differs by 3, preferably 2, more preferably 1 amino acid(s) from the hypervariable region of CDR3-x as shown in SEQ ID NO: 13; and said binding IL-17 molecule comprising in sequence the hypervariable regions CDR1$_i$-x, CDR2$_i$-x, and CDR3$_i$-x is capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

Similarly, an IL-17 binding molecule of the invention may be an IL-17 binding molecule which comprises at least one antigen binding site comprising at least one immunoglobulin light chain variable domain (V$_L$) which comprises in sequence a) hypervariable regions CDR'1 (SEQ ID NO: 4), CDR'2 (SEQ ID NO: 5) and CDR'3 (SEQ ID NO: 6); or b) hypervariable regions CDR1'$_i$, CDR2'$_i$, CDR3'$_i$, said hypervariable region CDR'1$_i$ differs by 3, preferably 2, more preferably 1 amino acid(s) from the hypervariable region of CDR'1 as shown in SEQ ID NO: 4, said hypervariable region CDR'2$_i$ differs by 3, preferably 2, more preferably 1 amino acid(s) from the hypervariable region of CDR'2 as shown in SEQ ID NO: 5; and said hypervariable region CDR'3$_i$ differs by 3, preferably 2, more preferably 1 amino acid(s) from the hypervariable region of CDR'3 as shown in SEQ ID NO: 6; and said binding IL-17 molecule comprises in sequence the hypervariable regions CDR'1$_i$, CDR'2$_i$, and CDR'3$_i$ is capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

Alternatively, an IL-17 binding molecule of the invention may be a IL-17 binding molecule comprising both heavy (V$_H$) and light chain (V$_L$) variable domains and said IL-17 binding molecule comprises at least one antigen binding site comprising:

a) an immunoglobulin heavy chain variable domain (V$_H$) which comprises in sequence hypervariable regions CDR1 (SEQ ID NO: 1), CDR2 (SEQ ID NO: 2) and CDR3 (SEQ ID NO: 3); and an immunoglobulin light chain variable domain (V$_L$) which comprises in sequence hypervariable regions CDR1' (SEQ ID NO: 4), CDR2' (SEQ ID NO: 5) and CDR3' (SEQ ID NO: 6); or b) an immunoglobulin heavy chain variable domain (V$_H$) which comprises in sequence hypervariable regions CDR1$_i$, CDR2$_i$, and CDR3$_i$, said hypervariable region hypervariable regions CDR1'$_i$, CDR2'$_i$, CDR3'$_i$, said hypervariable region CDR'1$_i$ differs by 3, preferably 2, more preferably 1 amino acid(s) from the hypervariable region of CDR1 as shown in SEQ ID NO: 1, said hypervariable region CDR2$_i$ differs by 3, preferably 2, more preferably 1 amino acid(s) from the hypervariable region of CDR2 as shown in SEQ ID NO: 2; and said hypervariable region CDR3$_i$ differs by 3, preferably 2, more preferably 1 amino acid(s) from the hypervariable region of CDR3 as shown in SEQ ID NO: 3; and an immunoglobulin light chain variable domain (V$_L$) which comprises in sequence hypervariable regions CDR1'$_i$, CDR2'$_i$, CDR3'$_i$, said hypervariable region CDR'1$_i$ differs by 3, preferably 2, more preferably 1 amino acid(s) from the hypervariable region of CDR'1 as shown in SEQ ID NO: 4, said hypervariable region CDR'2$_i$ differs by 3, preferably 2, more preferably 1 amino acid(s) from the hypervariable region of CDR'2 as shown in SEQ ID NO: 5; and said hypervariable region CDR'3$_i$ differs by 3, preferably 2, more preferably 1 amino acid(s) from the hypervariable region of CDR'3 as shown in SEQ ID NO: 6; and said binding IL-17 molecule defined in b) comprises in sequence the hypervariable regions CDR1$_i$, CDR2$_i$, CDR3$_i$, CDR'1$_i$, CDR'2$_i$, and CDR'3$_i$ is capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

Alternatively, an IL-17 binding molecule of the invention may be a IL-17 binding molecule comprising both heavy (V$_H$) and light chain (V$_L$) variable domains and said IL-17 binding molecule comprises at least one antigen binding site comprising:

a) an immunoglobulin heavy chain variable domain (V$_H$) which comprises in sequence hypervariable regions CDR1-x (SEQ ID NO: 11), CDR2-x (SEQ ID NO: 12) and CDR3-x (SEQ ID NO: 13); and an immunoglobulin light chain variable domain (V$_L$) which comprises in sequence hypervariable regions CDR1' (SEQ ID NO: 4), CDR2' (SEQ ID NO: 5) and CDR3' (SEQ ID NO: 6); or b) an immunoglobulin heavy chain variable domain (V$_H$) which comprises in sequence hypervariable regions CDR1$_i$-x, CDR2$_i$-x, and CDR3$_i$-x, said hypervariable region hypervariable regions CDR1$_i$-x, CDR2$_i$-x, CDR3$_i$-x, said hypervariable region CDR1$_i$-x differs by 3, preferably 2, more preferably 1 amino acid(s) from the hypervariable region of CDR1-x as shown in SEQ ID NO: 11, said hypervariable region CDR2$_i$-x differs by 3, preferably 2, more preferably 1 amino acid(s) from the hypervariable region of CDR2-x as shown in SEQ ID NO: 12; and said hypervariable region CDR3$_i$-x differs by 3, preferably 2, more preferably 1 amino acid(s) from the hypervariable region of CDR3-x as shown in SEQ ID NO: 13; and an immunoglobulin light chain variable domain (V$_L$) which comprises in sequence hypervariable regions CDR1'$_i$, CDR2'$_i$, CDR3'$_i$, said hypervariable region CDR'1$_i$ differs by 3, preferably 2, more preferably 1 amino acid(s) from the hypervariable region of CDR'1 as shown in SEQ ID NO: 4, said hypervariable region CDR'2$_i$ differs by 3, preferably 2, more preferably 1 amino acid(s) from the hypervariable region of CDR'2 as shown in SEQ ID NO: 5; and said hypervariable region CDR'3$_i$ differs by 3, preferably 2, more preferably 1 amino acid(s) from the hypervariable region of CDR'3 as shown in SEQ ID NO: 6; and said binding IL-17 molecule defined in b) comprises in sequence the hypervariable regions CDR1$_i$, CDR2$_i$, CDR3$_i$, CDR'1$_i$, CDR'2$_i$, and CDR'3$_i$ is capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

The inhibition of the binding of IL-17 to its receptor may be conveniently tested in various assays including such assays are described hereinafter in the text. By the term "to the same extent" is meant that the reference and the equivalent molecules exhibit, on a statistical basis, essentially identical IL-17 inhibitory activity in one of the assays referred to herein (see Example 1). For example, IL-17 binding molecules of the invention typically have IC$_{50}$s for the inhibition of human IL-17 on IL-6 production induced by human IL-17 in human dermal fibroblasts which are within +/−x5, i.e. below 10 nM, more preferably 9, 8, 7, 6, 5, 4, 3 or 2 nM of that of, preferably substantially the same as, the $IC_{50}$ of the corresponding reference molecule when assayed as described in Example 1.

Alternatively, the assay used may be an assay of competitive inhibition of binding of IL-17 by soluble IL-17 receptors (e.g. the human IL-17 R/Fc constructs of Example 1) and the IL-17 binding molecules of the invention.

Most preferably, the human IL-17 antibody comprises at least
a) one heavy chain which comprises a variable domain having an amino acid sequence substantially identical to that shown in SEQ ID NO: 8 starting with the amino acid at position 1 and ending with the amino acid at position 127 and the constant part of a human heavy chain; and
b) one light chain which comprises a variable domain having an amino acid sequence substantially identical to that shown in SEQ ID NO: 10 starting with the amino acid at position 1 and ending with the amino acid at position 109 and the constant part of a human light chain.

The constant part of a human heavy chain may be of the $\gamma_1$, $\gamma_2$, $\gamma_3$, $\gamma_4$, $\mu$, $\alpha_1$, $\alpha_2$, $\delta$ or $\epsilon$ type, preferably of the $\gamma$ type, more preferably of the $\gamma_1$ type, whereas the constant part of a human light chain may be of the $\kappa$ or $\lambda$ type (which includes the $\lambda_1$, $\lambda_2$ and $\lambda_3$ subtypes) but is preferably of the $\kappa$ type. The amino acid sequences of all these constant parts are given in Kabat et al (supra).

Conjugates of the binding molecules of the invention, e.g. enzyme or toxin or radioisotope conjugates, are also included within the scope of the invention.

"Polypeptide", if not otherwise specified herein, includes any peptide or protein comprising amino acids joined to each other by peptide bonds, having an amino acid sequence starting at the N-terminal extremity and ending at the C-terminal extremity. Preferably the polypeptide of the present invention is a monoclonal antibody, more preferred is a chimeric (also called V-grafted) or humanised (also called CDR-grafted) monoclonal antibody, most preferred a fully human antibody obtainable e.g. by the technology exemplified in Example 1. The humanised (CDR-grafted) or fully human monoclonal antibody may or may not include further mutations introduced into the framework (FR) sequences of the acceptor antibody.

A functional derivative of a polypeptide as used herein includes a molecule having a qualitative biological activity in common with a polypeptide to the present invention, i.e. having the ability to bind to the human IL-17. A functional derivative includes fragments and peptide analogs of a polpypeptide according to the present invention. Fragments comprise regions within the sequence of a polypeptide according to the present invention, e.g. of a specified sequence. The term "derivative" is used to define amino acid sequence variants, and covalent modifications of a polypeptide according to the present invention. e.g. of a specified sequence. The functional derivatives of a polypeptide according to the present invention, e.g. of a specified sequence, e.g. of the hypervariable region of the light and the heavy chain, preferably have at least about 65%, more preferably at least about 75%, even more preferably at least about 85%, most preferably at least about 95, 96, 97, 98, 99% overall sequence homology with the amino acid sequence of a polypeptide according to the present invention, e.g. of a specified sequence, and substantially retain the ability to bind the human IL-17 or e.g. neutralize IL-6 production of IL-17 induced human dermal fibroblasts.

The term "covalent modification" includes modifications of a polypeptide according to the present invention, e.g. of a specified sequence; or a fragment thereof with an organic proteinaceous or non-proteinaceous derivatizing agent, fusions to heterologous polypeptide sequences, and post-translational modifications. Covalent modified polypeptides, e.g. of a specified sequence, still have the ability to bind the human IL-17 or e.g. neutralize IL-6 production of IL-17 induced human dermal fibroblasts by crosslinking. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deaminated under mildly acidic conditions. Other post-translational modifications include hydroxylation of proline and lysine, phosphorylation of hydroxyl groups of seryl, tyrosine or threonyl residues, methylation of the $\alpha$-amino groups of lysine, arginine, and histidine side chains, see e.g. T. E. Creighton, Proteins: Structure and Molecular Properties, W. H. Freeman & Co., San Francisco, pp. 79-86 (1983). Covalent modifications e.g. include fusion proteins comprising a polypeptide according to the present invention, e.g. of a specified sequence and their amino acid sequence variants, such as immunoadhesins, and N-terminal fusions to heterologous signal sequences.

"Homology" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology. Methods and computer programs for the alignment are well known.

"Amino acid(s)" refer to all naturally occurring L-$\alpha$-amino acids, e.g. and including D-amino acids. The amino acids are identified by either the well known single-letter or three-letter designations.

The term "amino acid sequence variant" refers to molecules with some differences in their amino acid sequences as compared to a polypeptide according to the present invention, e.g. of a specified sequence. Amino acid sequence variants of a polypeptide according to the present invention, e.g. of a specified sequence, still have the ability to bind the human IL-17 or e.g. neutralize IL-6 production of IL-17 induced human dermal fibroblasts. Substitutional variants are those that have at least one amino acid residue removed and a different amino acid inserted in its place at the same position in a polypeptide according to the present invention, e.g. of a specified sequence. These substitutions may be single, where only one amino acid in the molecule has been substituted, or they may be multiple, where two or more amino acids have been substituted in the same molecule. Insertional variants are those with one or more amino acids inserted immediately adjacent to an amino acid at a particular position in a polypeptide according to the present invention, e.g. of a specified sequence. Immediately adjacent to an amino acid means connected to either the $\alpha$-carboxy or $\alpha$-amino functional group of the amino acid. Deletional variants are those with one or more amino acids in a polypeptide according to the present invention, e.g. of a specified sequence, removed. Ordinarily, deletional variants will have one or two amino acids deleted in a particular region of the molecule.

An IL-17 binding molecule of the invention may be produced by recombinant DNA techniques. In view of this, one or more DNA molecules encoding the binding molecule must be constructed, placed under appropriate control sequences and transferred into a suitable host organism for expression.

In a very general manner, there are accordingly provided
(i) DNA molecules encoding a single domain IL-17 binding molecule of the invention, a single chain IL-17 binding molecule of the invention, an IL-17 binding molecule comprising a heavy and light chain as defined herein, or fragments of a IL-17 binding molecule of the invention; and
(ii) the use of the DNA molecules of the invention for the production of a IL-17 binding molecule of the invention by recombinant means.

Accordingly, the invention provides a DNA molecule encoding an IL-17 binding molecule as described above.

Furthermore, the invention provides a DNA construct comprising a DNA molecule which is substantially homologous to SEQ ID NO: 7 or SEQ ID NO: 9.

Furthermore, the invention provides a DNA construct comprising two DNA molecules of which one is substantially homologous to SEQ ID NO: 7 or is a direct $DNA_H$ equivalent thereof and the other substantially homologous to SEQ ID NO: 9, or is a direct $DNA_L$ equivalent thereof.

The present state of the art is such that the skilled worker in the art is able to synthesize the DNA molecules of the invention given the information provided herein i.e. the amino acid sequences of the hypervariable regions and the DNA sequences coding for them. A method for constructing a variable domain gene is for example described in EPA 239 400 and may be briefly summarized as follows: A gene encoding a variable domain of a MAb of whatever specificity is cloned. The DNA segments encoding the framework and hypervariable regions are determined and the DNA segments encoding the hypervariable regions are removed so that the DNA segments encoding the framework regions are fused together with suitable restriction sites at the junctions. The restriction sites may be generated at the appropriate positions by mutagenesis of the DNA molecule by standard procedures. Double stranded synthetic CDR cassettes are prepared by DNA synthesis according to the sequences encoding for SEQ ID NO: 1 (CDR1), SEQ ID NO: 2 (CDR2), SEQ ID NO: 3 (CDR3), SEQ ID NO: 4 (CDR1'), SEQ ID NO: 5 (CDR2'), SEQ ID NO: 6 (CDR6'), SEQ ID NO: 11 (CDR1-x), SEQ ID NO: 12 (CDR2-x), SEQ ID NO: 13 (CDR3-x). These cassettes are provided with sticky ends so that they can be ligated at the junctions of the framework Furthermore, it is not necessary to have access to the mRNA from a producing hybridoma cell line in order to obtain a DNA construct coding for the IL-17 binding molecules of the invention. Thus PCT application WO 90/07861 gives full instructions for the production of an antibody by recombinant DNA techniques given only written information as to the nucleotide sequence of the gene. The method comprises the synthesis of a number of oligonucleotides, their amplification by the PCR method, and their splicing to give the desired DNA sequence.

Expression vectors comprising a suitable promoter or genes encoding heavy and light chain constant parts are publicly available. Thus, once a DNA molecule of the invention is prepared it may be conveniently transferred in an appropriate expression vector. DNA molecules encoding single chain antibodies may also be prepared by standard methods, for example, as described in WO 88/1649.

In analogy to the case for CDR equivalents, the term "direct $DNA_H$ equivalents thereof" is meant to stand for a first DNA construct encoding a heavy chain or fragment thereof of an IL-17 binding molecule of the invention and comprises:
a) a first part which encodes a variable domain comprising alternatively framework and hypervariable regions, said hypervariable regions being in sequence $CDR1_i$, $CDR2_i$ and $CDR3_i$, said $CDR1_i$ is at least 50% homologous, preferably at least 60, 70, 80, 85, or 90% homologous, more preferably at least 95% homologous to the hypervariable region CDR1 as shown in SEQ ID NO: 1, said CDR2i is at least 50% homologous, preferably at least 60, 70, 80, 85, or 90% homologous, more preferably at least 95% homologous to the hypervariable region CDR2 as shown in SEQ ID NO: 2, and $CDR3_i$ is at least 50% homologous, preferably at least 60, 70, 80, 85, or 90% homologous, more preferably at least 95% homologous to the hypervariable region CDR3 as shown in SEQ ID NO: 3; this first part starting with a codon encoding the first amino acid of the variable domain and ending with a codon encoding the last amino acid of the variable domain; and
b) a second part encoding a heavy chain constant part or fragment thereof which starts with a codon encoding the first amino acid of the constant part of the heavy chain and ends with a codon encoding the last amino acid of the constant part or fragment thereof, followed by a stop codon; and
c) said DNA construct encoding for a polypeptide which is capable either alone or in combination with another polypeptide of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

Similarly, the term "direct $DNA_H$-X equivalents thereof" is meant to stand for a first alternative DNA construct encoding a heavy chain or fragment thereof of an IL-17 binding molecule of the invention and comprises:
a) a first part which encodes a variable domain comprising alternatively framework and hypervariable regions, said hypervariable regions being in sequence $CDR1_i$-x, $CDR2_i$-x and $CDR3_i$-x, said $CDR1_i$-x is at least 50% homologous, preferably at least 60, 70, 80, 85, or 90% homologous, more preferably at least 95% homologous to the hypervariable region CDR1 as shown in SEQ ID NO: 11, said $CDR2_i$-x is at least 50% homologous, preferably at least 60, 70, 80, 85, or 90% homologous, more preferably at least 95% homologous to the hypervariable region CDR2 as shown in SEQ ID NO: 12, and $CDR3_i$-x is at least 50% homologous, preferably at least 60, 70, 80, 85, or 90% homologous, more preferably at least 95% homologous to the hypervariable region CDR3 as shown in SEQ ID NO: 13; this first part starting with a codon encoding the first amino acid of the variable domain and ending with a codon encoding the last amino acid of the variable domain; and
b) a second part encoding a heavy chain constant part or fragment thereof which starts with a codon encoding the first amino acid of the constant part of the heavy chain and ends with a codon encoding the last amino acid of the constant part or fragment thereof, followed by a stop codon; and
c) said DNA construct encoding for a polypeptide which is capable either alone or in combination with another polypeptide of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 inhuman dermal fibroblasts.

Preferably, these DNA constructs encode a variable domain comprising alternatively framework and hypervariable regions, said hypervariable regions being in sequence CDR1, CDR2 and CDR3, said CDR1 having the amino acid sequence SEQ ID NO: 1, said CDR2 having the amino acid sequence SEQ ID NO: 2, and said CDR3 having the amino acid sequence SEQ ID NO: 3. More preferably, these DNA constructs encode a variable domain comprising alternatively framework and hypervariable regions, said hypervariable regions being in sequence CDR1-x, CDR2-x and CDR3-x, said CDR1-x having the amino acid sequence SEQ ID NO: 11, said CDR2-x having the amino acid sequence SEQ ID NO: 12, and said CDR3-x having the amino acid sequence SEQ ID NO: 13. More preferably, this first part encodes a variable domain having an amino acid sequence substantially identical to the amino acid sequence as shown in SEQ ID NO: 8 starting with the amino acid at position 1 and ending with the amino acid at position 127. More preferably the first part has the nucleotide sequence as shown in SEQ ID NO: 7 starting with the nucleotide at position 1 and ending with the nucleotide at position 381. Also preferably, the second part encodes the constant part of a human heavy chain, more preferably the constant part of the human γ1 chain. This second part may be a DNA fragment of genomic origin (comprising introns) or a cDNA fragment (without introns).

Similarly, the term "direct $DNA_L$ equivalents thereof" is meant to stand for a second DNA construct encoding a light chain or fragment thereof of an IL-17 binding molecule of the invention and comprises:

a) a first part which encodes a variable domain comprising alternatively framework and hypervariable regions; said hypervariable regions being $CDR3_i'$ and optionally $CDR1_i'$ and $CDR2_i'$, said $CDR1_i'$ is at least 50% homologous, preferably at least 60, 70, 80, 85, or 90% homologous, more preferably at least 95% homologous to the hypervariable region CDR1' as shown in SEQ ID NO: 4, said $CDR2_i'$ is at least 50% homologous, preferably at least 60, 70, 80, 85, or 90% homologous, more preferably at least 95% homologous to the hypervariable region CDR2' as shown in SEQ ID NO: 5, and said $CDR3_i'$ is at least 50% homologous, preferably at least 60, 70, 80, 85, or 90% homologous, more preferably at least 95% homologous to the hypervariable region CDR3' as shown in SEQ ID NO: 6; this first part starting with a codon encoding the first amino acid of the variable domain and ending with a codon encoding the last amino acid of the variable domain; and b) a second part encoding a light chain constant part or fragment thereof which starts with a codon encoding the first amino acid of the constant part of the light chain and ends with a codon encoding the last amino acid of the constant part or fragment thereof followed by a stop codon; and c) said DNA construct encoding for a polypeptide which is capable either alone or in combination with another polypeptide of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

Preferably, this second DNA construct encodes a variable domain comprising alternatively framework and hypervariable regions, said hypervariable regions being in sequence CDR1', CDR2' and CDR3', said CDR1' having the amino acid sequence SEQ ID NO: 4, said CDR2' having the amino acid sequence SEQ ID NO: 5, and said CDR3' having the amino acid sequence SEQ ID NO: 6. More preferably, this first part of the second DNA construct encodes a variable domain having an amino acid sequence substantially identical to the amino acid sequence as shown in SEQ ID NO: 10 starting with the amino acid at position 1 and ending with the amino acid at position 109. More preferably, the first part has the nucleotide sequence as shown in SEQ ID NO: 9 starting with the nucleotide at position 1 and ending with the nucleotide at position 327. Also preferably the second part encodes the constant part of a human light chain, more preferably the constant part of the human κ

Preferably, the first and second DNA construct will be used together, but may be also used separately.

The invention also includes IL-17 binding molecules in which one or more of the amino acid residues of CDR1, CDR2, CDR3, CDR1-x, CDR2-x, CDR3-x, CDR1', CDR2' or CDR3' or the frameworks, typically only a few (e.g. 1-4), are changed; for instance by mutation e.g. site directed mutagenesis of the corresponding DNA sequences. The invention includes the DNA sequences coding for such changed IL-17 binding molecules. In particular the invention includes IL-17 binding molecules in which one or more residues of CDR1' or CDR2' have been changed from the residues shown in SEQ ID NO: 4 (for CDR1') and SEQ ID NO: 5 (for CDR2').

In the first and second DNA constructs, the first and second parts may be separated by an intron, and, an enhancer may be conveniently located in the intron between the first and second parts. The presence of such an enhancer which is transcribed but not translated, may assist in efficient transcription. In particular embodiments the first and second DNA constructs comprise the enhancer of a heavy chain gene advantageously of human origin.

Each of the DNA constructs are placed under the control of suitable control sequences, in particular under the control of a suitable promoter. Any kind of promoter may be used, provided that it is adapted to the host organism in which the DNA constructs will be transferred for expression.

The desired antibody may be produced in a cell culture or in a transgenic animal. A suitable transgenic animal may be obtained according to standard methods which include micro injecting into eggs the first and second DNA constructs placed under suitable control sequences transferring the so prepared eggs into appropriate pseudo-pregnant females and selecting a descendant expressing the desired antibody.

When the antibody chains are produced in a cell culture, the DNA constructs must first be inserted into either a single expression vector or into two separate but compatible expression vectors, the latter possibility being preferred.

Accordingly, the invention also provides an expression vector able to replicate in a prokaryotic or eukaryotic cell line which comprises at least one of the DNA constructs above described.

Each expression vector containing a DNA construct is then transferred into a suitable host organism. When the DNA constructs are separately inserted on two expression vectors, they may be transferred separately, i.e. one type of vector per cell, or co-transferred, this latter possibility being preferred. A suitable host organism may be a bacterium, a yeast or a mammalian cell line, this latter being preferred. More preferably, the mammalian cell line is of lymphoid origin, e.g. a myeloma, hybridoma or a normal immortalised B-cell, which conveniently does not express any endogenous antibody heavy or light chain.

For expression in mammalian cells it is preferred that the IL-17 binding molecule coding sequence is integrated into the host cell DNA within a locus which permits or favours high level expression of the IL-17 binding molecule. Cells in which the IL-17 binding molecule coding sequence is integrated into such favourable loci may be identified and selected on the basis of the levels of the IL-17 binding molecule which they express. Any suitable selectable marker may be used for preparation of host cells containing the IL-17 binding molecule coding sequence; for instance, a dhfr gene/methotrexate or equivalent selection system may be used. Alternative systems for expression of the IL-17 binding molecules of the invention include GS-based amplification/selection systems, such as those described in EP 0256055 B, EP 0323997 B and European patent application 89303964.4.

In a further aspect of the invention there is provided a process for the product of an IL-17 binding molecule which comprises (i) culturing an organism which is transformed with an expression vector as defined above and (ii) recovering the IL-17 binding molecule from the culture.

For the purposes of the present description an antibody is "capable of inhibiting the binding of IL-17 as AIN457" if the antibody is capable of inhibiting the binding of IL-17 to its receptor substantially to the same extent as the AIN457 antibody, wherein "to the same extent" has meaning as defined above.

The AIN457 antibody has binding affinity for IL-17 which is higher than affinities previously reported for anti-IL-17 antibodies, in particular to any anti human IL-17 antibodies. Thus AIN457 has a dissociation equilibrium constant $K_D$ for binding to IL-17 of about 0.188±0.036 nM (determined by BIAcore, e.g. as shown in Example 2). This high binding affinity makes the AIN457 antibody particularly suitable for therapeutic applications.

In the present description the phrase "Il-17 mediated disease" encompasses all diseases and medical conditions in which IL-17 plays a role, whether directly or indirectly, in the disease or medical condition, including the causation, development, progress, persistence or pathology of the disease or condition.

In the present description the terms "treatment" or "treat" refer to both prophylactic or preventative treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse.

IL-17 binding molecules as defined above which have binding specificity for human IL-17, in particular antibodies which are capable of inhibiting the binding of IL-17 to its receptor; and antibodies to IL-17 which are capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts, are herein referred to as Antibodies of the Invention.

Preferably the Antibodies of the Invention are human antibodies, most preferably the AIN457 antibody or direct equivalents thereof.

The Antibodies of the Invention block the effects of IL-17 on its target cells and thus are indicated for use in the treatment of IL-17 mediated diseases and disorders. These and other pharmacological activities of the Antibodies of the Invention may be demonstrated in standard test methods for example as described below:

Neutralization of IL-17 Dependent Production of Interleukin-6 by Primary Human Fibroblasts:

The production of IL-6 in primary human (dermal) fibroblasts is dependent on IL-17 (Hwang SY et al., (2004) Arthritis Res Ther; 6:R120-128.

In short, human dermal fibroblasts are stimulated with recombinant IL-17 in the presence of various concentrations of Antibody of the Invention or human IL-17 receptor with Fc part. The chimeric anti-CD25 antibody Simulect® (basiliximab) is used as a negative control. Supernatant is taken after 16 h stimulation and assayed for IL-6 by ELISA. Antibodies of the Invention typically have $IC_{50}$s for inhibition of IL-6 production (in the presence 1 nM human IL-17) of about 50 nM or less (e.g. from about 0.01 to about 50 nM) when tested as above, i.e. said inhibitory activity is measured on IL-6 production induced by hu-IL-17 in human dermal fibroblasts. Preferably, the Antibodies of the Invention have an $IC_{50}$ for inhibition of IL-6 production as defined above of about 20 nM or less, more preferably of about 10 nM or less, more preferably of about 5 nM or less, more preferably of about 2 nM or less, more preferably of about 1 nM or less.

As indicated in the above assay Antibodies of the Invention potently block the effects of IL-17. Accordingly, the Antibodies of the Invention have pharmaceutical utility as follows:

Antibodies of the Invention are useful for the prophylaxis and treatment of IL-17 mediated diseases or medical conditions, e.g. inflammatory conditions, allergies and allergic conditions, hypersensitivity reactions, autoimmune diseases, severe infections, and organ or tissue transplant rejection.

For example, Antibodies of the Invention may be use for the treatment of recipients of heart, lung, combined heart-lung, liver, kidney, pancreatic, skin or corneal transplants, including allograft rejection or xenograft rejection, and for the prevention of graft-versus-host disease, such as following bone marrow transplant, and organ transplant associated arteriosclerosis.

Antibodies of the Invention are particularly useful for the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarhropathies including ankolsing spondylitis, Reiter syndrome, reactive arthritis, psoriatic arthritis, and enterophathis arthritis, hypersensitivity (including both airways hypersensitivity and dermal hypersensitivity) and allergies. Specific auto-immune diseases for which Antibodies of the Invention may be employed include autoimmune haematological disorders (including e.g. hemolytic anaemia, aplastic anaemia, pure red cell anaemia and idiopathic thrombocytopenia), systemic lupus erythematosus, inflammatory muscle disorders, polychondritis, sclerodoma, Wegener granulomatosis, dermatomyositis, chronic active hepatitis, myasthenia gravis, psoriasis, Steven-Johnson syndrome, idiopathic sprue, autoimmune inflammatory bowel disease (including e.g. ulcerative colitis, Crohn's disease and Irritable Bowel Syndrome), endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy), tumors, multiple sclerosis, inflammatory disease of skin and cornea, myositis, loosening of bone implants, metabolic disorders, such as atherosclerosis, diabetes, and dislipidemia.

Antibodies of the Invention are also useful for the treatment, prevention, or amelioration of asthma, bronchitis, pneumoconiosis, pulmonary emphysema, and other obstructive or inflammatory diseases of the airways.

Antibodies of the Invention are useful for treating undesirable acute and hyperacute inflammatory reactions which are mediated by IL-17 or involve IL-17 production, or the promotion of TNF release by IL-17, e.g. acute infections, for example septic shock (e.g., endotoxic shock and adult respiratory distress syndrome), meningitis, pneumonia; and severe burns; and for the treatment of cachexia or wasting syndrome associated with morbid TNF release, consequent to infection, cancer, or organ dysfunction, especially AIDS-related cachexia, e.g., associated with or consequential to HIV infection.

Antibodies of the Invention are particularly useful for treating diseases of bone metabolism including osteoarthritis, osteoporosis and other inflammatory arthritides, and bone loss in general, including age-related bone loss, and in particular periodontal disease.

For these indications, the appropriate dosage will, of course, vary depending upon, for example, the particular Antibody of the Invention to be employed, the host, the mode of administration and the nature and severity of the condition being treated. However, in prophylactic use, satisfactory results are generally indicated to be obtained at dosages from about 0.05 mg to about 10 mg per kilogram body weight more usually from about 0.1 mg to about 5 mg per kilogram body weight. The frequency of dosing for prophylactic uses will normally be in the range from about once per week up to about once every 3 months, more usually in the range from about once every 2 weeks up to about once every 10 weeks, e.g. once every 4 to 8 weeks. Antibody of the Invention is conveniently administered parenterally, intravenously, e.g. into the antecubital or other peripheral vein, intramuscularly, or subcutaneously. A prophylactic treatment typically comprises administering the Antibody of the Invention once per month to once every 2 to 3 months, or less frequently.

The Antibodies of the Invention may be administered as the sole active ingredient or in conjunction with, e.g. as an adjuvant to or in combination to, other drugs e.g. immunosuppressive or immunomodulating agents or other anti-inflammatory agents, e.g. for the treatment or prevention of diseases mentioned above. For example, the Antibodies of the Invention may be used in combination with DMARD, e.g. Gold salts, sulphasalazine, antimalarias, methotrexate, D-penicillamine, azathioprine, mycophenolic acid, cyclosporine A, tacrolimus, sirolimus, minocycline, leflunomide, glococorticoids; a calcineurin inhibitor, e.g. cyclosporin A or FK 506; a modulator of lymphocyte recirculation, e.g. FTY720 and FTY720 analogs; a mTOR inhibitor, e.g. rapamycin, 40-O-(2-hydroxyethyl)-rapamycin, CCI779, ABT578, AP23573 or TAFA-93; an ascomycin having immuno-suppressive properties, e.g. ABT-281, ASM981, etc.; corticosteroids; cyclophos-phamide; azathioprene; methotrexate; leflunomide; mizoribine; mycophenolic acid; myco-pheno-late mofetil; 15-deoxyspergualine or an immunosuppressive homologue, analogue or derivative thereof; immunosuppressive monoclonal antibodies, e.g., monoclonal antibodies to leukocyte receptors, e.g., MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; anti TNF agents, e.g. monoclonal antibodies to TNF, e.g. infliximab, adalimumab, CDP870, or receptor constructs to TNF-RI or TNF-RII, e.g. Etanercept, PEG-TNF-RI; blockers of proinflammatory cytokines, IL-1 blockers, e.g. Anakinra or IL-1 trap, AAL160, ACZ 885, IL-6 blockers; chemokines blockers, e.g inhibitors or activators of proteases, e.g. metalloproteases, anti-IL-15 antibodies, anti-IL-6 antibodies, anti-CD20 antibodies, NSAIDs, such as aspirin or an anti-infectious agent (list not limited to the agent mentioned).

In accordance with the foregoing the present invention provides in a yet further aspect:

A method as defined above comprising co-administration, e.g. concomitantly or in sequence, of a therapeutically effective amount of an IL-17 binding molecule, e.g. an Antibody of the Invention, and at least one second drug substance, said second drug substance being a immuno-suppressive/immunomodulatory, anti-inflammatory chemotherapeutic or anti-infectious drug, e.g. as indicated above.

Or, a therapeutic combination, e.g. a kit, comprising of a therapeutically effective amount of a) an IL-17 binding molecule, e.g. an Antibody of the Invention, and b) at least one second substance selected from a immuno-suppressive/immunomodulatory, anti-inflammatory chemotherapeutic or anti-infectious drug, e.g. as indicated above. The kit may comprise instructions for its administration.

Where the Antibodies of the Invention are administered in conjunction with other immuno-suppressive/immunomodulatory, anti-inflammatory chemotherapeutic or anti-infectious therapy, dosages of the co-administered combination compound will of course vary depending on the type of co-drug employed, e.g. whether it is a DMARD, anti-TNF, IL-1 blocker or others, on the specific drug employed, on the condition being treated and so forth.

Pharmaceutical compositions of the invention may be manufactured in conventional manner. A composition according to the invention is preferably provided in lyophilized form. For immediate administration it is dissolved in a suitable aqueous carrier, for example sterile water for injection or sterile buffered physiological saline. If it is considered desirable to make up a solution of larger volume for administration by infusion rather as a bolus injection, it is advantageous to incorporate human serum albumin or the patient's own heparinised blood into the saline at the time of formulation. Alternatively, the formulation is given subcutaneous. The presence of an excess of such physiologically inert protein prevents loss of antibody by adsorption onto the walls of the container and tubing used with the infusion solution. If albumin is used, a suitable concentration is from 0.5 to 4.5% by weight of the saline solution. Other formulations comprise liquid or lyophilized formulation.

The invention is further described by way of illustration in the following Examples.

EXAMPLES

Transgenic mice engineered to express the human IgG/κ repertoire instead of the murine immunoglobulin repertoire (Fishwild et al., 1996, Nat Biotechnol., 14, 845-851) are used to generate antibodies to human IL-17. B cells from these mice are immortalized by standard hybridoma technology and murine hybridoma cells are obtained which secrete the human IgG1/κ antibody AIN457.

Example 1

Generation of the Hybridoma, Purification of the Antibodies, Selection of AIN457 Antibody Production of recombinant human IL-17 (huIL-17): Recombinant huIL-17 is either produced in *E. coli* in inclusion bodies and refolded by conventional techniques (produced in house carrier free (*E. coli*; Novartis Pharma, batch BM-E3141/98) or bought (carrier free, *E. coli*; R&D Systems #317-IL/CF)) or as secreted and partially glycosylated protein in HEK.EBNA (Recombinant huIL-17, carrier free (IL-17 APP-C6 from transfected HEK/EBNA cells; Novartis Pharma, batch En.E-3382/82; 0.28 mg/ml; recombinant huIL-17, carrier free (IL-17 APP-C4 from transfected HEK/EBNA cells; Novartis Pharma, batch En.E-3382/83; 0.29 mg/ml)). The latter form features a C-terminal 4 amino acids extension for rapid purification from culture supernatants by immunoaffinity chromatography. In this case, culture supernatants are loaded on a column of appropriate size of a specific immobilized anti-tag antibody coupled to CNBr activated Sepharose 4B at a density of 10 mg/ml resin following the manufacturer's instructions (Pharmacia). After base-line washing with PBS, bound huIL-17 is eluted with 100 mM glycine, pH 2.7 and immediately neutralized with diluted NaOH.

Coupling of huIL-17 to Keyhole Limpet Hemocyanin (KLH): HuIL-17 produced in either *E. coli* or HEK.EBNA is coupled to KLH pre-activated with an excess of the homobifunctional cross-linker Disuccinimidyl suberate (DSS). Briefly, 20 mg lyophilized Imject® Mariculture KLH (Pierce # 77600) are reconstituted with 2 ml $H_2O$ to give a 10 mg/ml solution containing Phosphate Buffered Saline (PBS), pH 7.2. To this solution 400 μl of 250 mM DSS in Dimethyl Sulfoxide (DMSO) are added and the mixture stirred for about 1 hr at room temperature (not all the reagent dissolved and some precipitate formed). After a brief centrifugation and filtration (0.45 μm) the solution is then desalted on Sephadex G25 fine (Pharmacia) in PBS (flow rate 2 ml/min) yielding about 11 mg activated KLH at 1.5 mg/ml (Bradford). 1 ml of the activated KLH (1.5 mg) is mixed with 1 ml of a 9 mg/ml solution in water of lyophilyzed *E. coli* derived huIL-17 (batch BM-E3141/98). The solution remains clear and is incubated for 2 hrs at room temperature. The concentration of the resulting complex is 1.4 mg/ml (measured by Bradford). 1 ml of the activated KLH (1.5 mg) is mixed with 1 ml of HEK.EBNA huIL-17 (about 3 mg in water; batch En.E-3382/83). The solution remains clear and is incubated for 2 hrs at room temperature. Concentration (Bradford) is 2.9 mg/ml.

Immunization: The genetically engineered mouse 27340 (female; MEDAREX Inc, Annandale, N.J.) in which the murine immunoglobulin variable and constant part genes are functionally replaced by their human counterparts (Genotype Tg code 221100-TgH (CMD)++; TgN(Hco7)11952+; TgH (KD)++; TgN(KCO5)9272+ (see also Sherie L. Morrison, 1994, Nature, Vol. 368, p. 812-813; Nils Lonberg et al., 1994, Nature, Vol. 368, p. 856-859) is immunized following the scheme reported in table 1.

TABLE 1

Immunization schedule

| Day | Date | Immunogen | Dose and route of immunization |
|---|---|---|---|
| 0 | 07 Jun. 2001 | HuIL-17 (BM-E3141/98) coupled to KLH mixed 1:1 with huIL-17 (BM-E3141/98) in Gerbu adjuvant | 25 μg of each s.c. in two spots; total volume/mouse with adjuvant 100 μl |
| 14 | 21 Jun. 2001 (1$^{st}$ boost) | HuIL-17 (BM-E3141/98) coupled to KLH mixed 1:1 with huIL-17 (En.E-3382/83) coupled to KLH in Gerbu adjuvant | 25 μg of each s.c. in two spots; total volume/mouse with adjuvant 100 μl |
| 28 | 05 Jul. 2001 (2$^{nd}$ boost) | HuIL-17 (BM-E3141/98) mixed 1:1 with huIL-17 (En.E-3382/83) in Gerbu adjuvant | 10 μg of each s.c. in two spots; total volume/mouse with adjuvant 100 μl |
| 35 | 12 Jul. 2001 | | Sera collected for ELISA |
| 42 | 19 Jul. 2001 (3$^{rd}$ boost) | HuIL-17 (BM-E3141/98) mixed 1:1 with huIL-17 (En.E-3382/83) coupled to KLH in Gerbu adjuvant | 20 μg of each s.c. in two spots; total volume/mouse with adjuvant 100 μl |
| 63 | 09 Aug. 2001 (4$^{th}$ boost) | HuIL-17 (BM-E3141/98) coupled to KLH mixed 1:1 with huIL-17 (En.E-3382/83) coupled to KLH in Gerbu adjuvant | 20 μg of each s.c. in two spots; total volume/mouse with adjuvant 100 μl |
| 91 | 06 Sep. 2001 (5$^{th}$ boost) | HuIL-17 (BM-E3141/98) mixed 1:1 with huIL-17 (En.E-3382/83) in Gerbu adjuvant | 20 μg of each s.c. in two spots; total volume/mouse with adjuvant 100 μl |
| 99 | 14 Sep. 2001 | | Sera collected for ELISA |
| 117 | 02 Oct. 2001 | HuIL-17 (En.E-3382/83) HuIL-17 (En.E-3382/83) coupled to KLH | 10 μg/mouse i.v. 10 μg/mouse i.p. |
| 118 | 03 Oct. 2001 | HuIL-17 (En.E-3382/83) coupled to KLH | 10 μg/mouse i.p. |
| 119 | 04 Oct. 2001 | HuIL-17 (En.E-3382/83) coupled to KLH | 10 μg/mouse i.p. |
| 120 | 05 Oct. 2001 | fusion | |

Sera samples are obtained 35 and 99 days after the start of the immunization protocol, for measuring levels of anti-huIL17 antibody by enzyme-linked immunosorbent assay (ELISA).

Generation of hybridomas: On day 120, mouse 27340 is killed by $CO_2$ inhalation. Total spleen cells ($1 \times 10^8$) are fused with PAI-0 cells ($5 \times 10^7$ cells) using PEG 4000. Fused cells are plated out in 720 wells (1 ml/well), containing a feeder layer of mouse peritoneal cells (Balb/c mice), in HAT medium (RPMI 1640 containing 2 g/l Sodium Bicarbonate, $5 \times 10^{-5}$ M β-Mercaptoethanol, $10^{-4}$ M Hypoxanthine, $1.6 \times 10^{-5}$ M Thymidine, $4 \times 10^{-7}$ M Aminopterin, 10% heat inactivated FCS and 50 μg/ml Gentamycin). At day 14, HAT medium is exchanged with HT medium i.e. HAT medium without Aminopterin. Screening starts on day 10, and lasts two weeks. Of the initial 720 wells plated, 684 wells (95%) are positive for hybridoma growth. Supernatants are collected and screened for huIL-17 reactive MAb in ELISA using both the *E. coli* and the HEK/EBNA derived huIL-17. Fifty-two primary wells score positive for the presence of anti-huIL-17 antibodies. Twenty-eight hybridomas are cloned and the remaining ones are frozen. Cloning is done, in 4×96 well microtiter plates, in HT medium and a feeder layer of mouse peritoneal cells. Hybridomas are plated at 0.5 cell/100 µl per well. Wells are screened microscopically for growth, and positive ones are fed 100 µl of HT medium. The following day, supernatants are tested for antibody production in a huIL-17 specific ELISA. Upon cloning, the majority of the cloned hybridomas retain the capacity to secrete anti-huIL-17 specific Monoclonal Antibody (MAb).

Production and purification of antibody: The selected clones are transferred in serum free medium (5 ml) into 25 cm² TC (TC: tissue culture) flasks. Hybridomas are progressively expanded in serum free medium to 75 cm² TC flasks and roller flasks. All the different anti-hu-IL-17 MAb including NVP-AIN457-NX (340-110-28 i.e. mouse number-hybridoma number-clone number) are purified by Protein A affinity chromatography. Culture supernatants are adjusted to pH 7.3 and loaded on a column of appropriate size of Protein A Sepharose 4 fast flow (Pharmacia). After base-line washing with 100 mM phosphate buffer, pH 7.3 bound antibodies are eluted with 50 mM citrate, pH 2.7, 140 mM NaCl. The eluted fraction is immediately neutralized (pH 7.0) and sterile filtered. Protein concentration is determined by absorption at 280 nm using a factor of 1.35 Absorption Unit (AU)/mg.

Inhibitory activity of anti-huIL-17 MAb on IL-6 production induced by huIL-17 in human dermal fibroblasts: Human dermal fibroblasts are cultured in FBM supplemented with 2% FCS, insulin (5 µg/ml) huFGF-basic (0.1 µg/ml) and Gentamycin (50 µg/ml). The fibroblasts are detached from plastic using a Trypsin/EDTA solution. Fibroblasts are distributed into 96 well microtiter plates at a density of 1×10⁴ cells/well in FBM supplemented with 1% FCS. Fibroblasts are allowed to adhere to the plates overnight. The next morning medium is removed and fresh FBM supplemented with 1% FCS, huIL-17 (different concentrations ranging from 30 to 500 ng/ml) and hybridoma supernatants (⅕ final dilution) or purified antibodies are added to a final volume of 200 µl. Culture supernatants are collected after an incubation of 24 h and huIL-6 production is measured by ELISA.

ELISA for detection of anti-huIL-17 antibodies: ELISA microtiter plates are coated with recombinant huIL-17 (100 µl/well at 3 µg/ml; batch BM-E3141/98 or En.E-3382/82) in PBS 0.02% NaN₃ and incubated overnight at room temperature. The following day, microtiter plates are blocked with 300 µl of PBS/2% BSA/0.02% NaN₃ for 2 h at 37° C. Plates are then washed 4 times with PBS/0.05% Tween 20/0.02% NaN₃. Serum dilutions of mouse 27340 (final dilution range at day 35: 1/100 to 1/3200; final dilution range at day 99: 1/200 to 1/12800; 100 µl/well) or culture supernatants of hybridomas (final dilution 1:3; 100 µl/well) are added. After an overnight incubation at room temperature, plates are washed 4 times with PBS/0.05% Tween 20/0.02% NaN₃. A biotin-conjugated mouse anti-hu-IgG, Fc fragment specific antibody is added at a final dilution of 1/20000 (100 µl/well). Samples are left to react for 4 h at room temperature. After washing (4 times), alkaline phosphatase-conjugated streptavidin is added at a final dilution of 1/8000 (100 µl/well). After 40 minutes at room temperature, plates are washed again 4 times and the substrate (p-nitrophenylphosphate in diethylamino buffer pH 9.8; 150 µl/well) is added. Plates are read after 30 or 45 min depending on the development of the reaction in a microtiter reader (Bio-Rad) using filters of 405 and 490 nm.

ELISA for detection of antibody isotype: For revealing the isotype of the MAb, culture supernatants (100 µl; final dilution ⅕) are added to the wells of microtiter plates coated with huIL-17 (see above), and incubated overnight at room temperature. After washing (4 times), 100 µl/well of biotin-conjugated mouse MAbs anti-human IgG1 (final dilution 1/1000), IgG2 (final dilution 1/1000), IgG3 (final dilution 1/1000) IgG4 (final dilution 1/2000) or anti human κ light chain (final dilution 1/1000) are added for 4 h at room temperature. As a control a biotin-conjugated rat anti-mouse λ1 and λ2 light chain specific MAb is used (final dilution 1/1000). This is followed as previously described by washing and addition of alkaline phosphatase-conjugated streptavidin (100 µl; final dilution 1/8000). After washing (4 times) the substrate (p-nitrophenylphosphate in diethylamino buffer; 100 µl) is added. Plates are read after 30 or 45 min depending on development of reaction, in a microtiter reader (Bio-Rad) using filters of 405 and 490 nm.

ELISA for detection of huIL-6 production: ELISA microtiter plates are coated with an anti-huIL-6 mouse MAb (MAB206 from R&D system; 100 µl/well at 4 µg/ml) in PBS 0.02% NaN₃ and incubated overnight at room temperature. The following day, microtiter plates were blocked with 300 µl of PBS/2% BSA/0.02% NaN₃ for 2 h at 37° C. Plates were then washed 4 times with PBS/0.05% Tween 20/0.02% NaN₃. Culture supernatants of human dermal fibroblasts (final dilution 1:3; 100 µl/well) were added. To establish a titration curve huIL-6 (100 µl/well) is titrated from 400 pg/ml to 3.1 pg/ml in 1:2 dilution steps. After an overnight incubation at room temperature, plates are washed 4 times with PBS/0.05% Tween 20/0.02% NaN₃. A biotin-conjugated goat anti-huIL-6 antibody (BAP206; R&D Systems) is added (25 ng/ml; 100 µl/well). Samples are left to react for 4 h at room temperature. After washing (4 times), alkaline phosphatase-conjugated streptavidin is added at a final dilution of 1/8000 (100 µl/well). After 40 minutes at room temperature, plates are washed again 4 times and the substrate (p-nitrophenylphosphate in diethylamino buffer pH 9.8; 150 µl/well) is added. Plates are read after 30 min in a microtiter reader (Bio-Rad) using filters of 405 and 490 nm.

Calculations: Values are reported as original O.D. values or as % inhibition calculated on the means of duplicate values. Additional data are reported as Means±SEM. An huIL-6 standard curve was used to measure huIL-6 concentration in culture supernatants by using a cubic curve fit.

Results

Serum Titers of Mouse 27340:

TABLE 2

Anti-huIL-17 serum titers (mouse 27340)

| Day | HuIL-17 batch* | Serum dilution O.D. values (Means ± SEM) | | | | | | |
|---|---|---|---|---|---|---|---|---|
| | | 1:100 | 1:200 | 1:400 | 1:800 | 1:1600 | 1:3200 | 1:6400 | 1:12800 |
| 35 | E. coli | 1.795 ± 0.022 | 1.524 ± 0.006 | 1.167 ± 0.015 | 0.854 ± 0.013 | 0.615 ± 0.005 | 0.378 ± 0.032 | | |
| | HEK/EBNA | 2.180 ± 0.041 | 1.875 ± 0.005 | 1.577 ± 0.047 | 1.313 ± 0.016 | 1.031 ± 0.011 | 0.728 ± 0.003 | | |
| 99 | E. coli | | 2.130 ± 0.078 | 1.913 ± 0.075 | 1.635 ± 0.041 | 1.494 ± 0.066 | 1.125 ± 0.001 | 0.810 ± 0.070 | 0.559 ± 0.021 |
| | HEK/EBNA | | 2.029 ± 0.005 | 1.925 ± 0.030 | 1.716 ± 0.012 | 1.524 ± 0.004 | 1.259 ± 0.018 | 0.970 ± 0.036 | 0.706 ± 0.002 |

*Microtiter plates were coated with huIL-17 (3 µg/ml) from E. coli (BM-E3141/98) or HEK/EBNA cells (En.E-3382/82).

The serum of mouse 27340 is analyzed in ELISA for the presence of anti-huIL-17 antibodies on days 35 and 99 on two different preparations of huIL-17 (Table 2). Results show that serum titers of mouse 27340 increase about fourfold between day 35 and day 99 and that both huIL-17 preparations are recognized.

Binding in ELISA of hybridoma supernatants: 684 supernatants are tested in ELISA for the presence of anti-huIL-17 antibodies, using two preparations of recombinant huIL-17, the former from E coli (BM-E3141/98) the latter from HEK/EBNA cells (En.E-3382/82). Fifty-two supernatants score positive for the presence of anti-huIL-17 antibodies (Table 3). Preferential binding to one or the other preparation of huIL-17 is observed in a few cases. The 28 hybridomas that are subsequently cloned are underlined.

TABLE 3

ELISA reactivity of culture supernatants

| Hybridoma (No) | E. coli O.D. values | HEK/EBNA O.D. values |
|---|---|---|
| | HuIL-17 batch* | |
| 1 | 1.935/1.830 | ND |
| 3 | 1.928/1.928 | 2.026/1.956 |
| 5 | 1.386/1.471 | 2.099/2.042 |
| 59 | 1.917/2.078 | 2.342/2.384 |
| 66 | 1.629/1.619 | ND |
| 104 | 2.650/2.716 | 2.439/2.366 |
| 106 | 1.329/1.371 | 1.362/1.465 |
| 110 | 2.355/2.363 | 2.425/2.497 |
| 112 | 0.789/0.857 | 1.154/1.208 |
| 116 | 1.656/1.652 | ND |
| 128 | 1.244/1.669 | 0.714/0.695 |
| 142 | 1.192/1.322 | 0.847/0.810 |
| 173 | 1.899/2.108 | 1.966/2.023 |
| 182 | 0.948/0.903 | 0.874/0.866 |
| 190 | 2.249/2.084 | 2.150/2.139 |
| 196 | 1.406/1.305 | 1.797/1.752 |
| 216 | 1.120/1.146 | 1.114/1.128 |
| 234 | 1.890/1.990 | ND |
| 277 | 1.674/1.640 | ND |
| 285 | 0.678/0.789 | 0.735/0.784 |
| 298 | 2.475/2.677 | 2.340/2.358 |
| 305 | 1.721/1.789 | 0.602/0.634 |
| 319 | 1.111/1.073 | 1.223/1.202 |
| 328 | 1.738/1.762 | 1.869/1.835 |
| 343 | 2.478/2.702 | 2.302/2.448 |
| 373 | 1.200/1.194 | 1.212/1.233 |
| 386 | 1.780/1.812 | 2.002/1.905 |
| 435 | 2.194/2.139 | 2.221/2.169 |
| 439 | 1.180/1.236 | 1.442/1.470 |
| 444 | 1.034/1.066 | 1.166/1.138 |
| 450 | 2.060/2.209 | 2.079/2.237 |
| 477 | 1.392/1.348 | 1.515/1.524 |
| 496 | 2.131/2.078 | 2.569/2.798 |
| 504 | 1.755/1.559 | ND |
| 543 | 2.332/2.455 | 2.370/2.381 |
| 544 | 1.145/1.196 | 1.187/1.201 |
| 548 | 0.728/0.750 | 0.891/0.909 |
| 552 | 0.824/0.811 | 0.969/0.943 |
| 557 | 2.241/2.326 | 2.347/2.483 |
| 564 | 0.628/0.675 | 0.808/0.820 |
| 566 | 1.092/1.068 | 1.239/1.152 |
| 577 | 1.018/0.928 | 1.226/1.206 |
| 597 | 0.781/0.821 | 1.117/1.121 |
| 612 | 1.935/1.777 | 2.033/1.989 |
| 622 | 2.121/2.230 | 2.592/2.277 |
| 627 | 1.000/1.077 | 1.203/1.209 |
| 649 | 1.335/1.389 | 1.311/1.337 |
| 658 | 1.218/1.297 | 1.415/1.437 |
| 674 | 1.112/1.087 | 1.134/1.127 |
| 686 | 1.447/1.549 | 1.730/1.646 |
| 705 | 1.899/1.803 | 1.870/1.872 |
| 720 | 2.249/2.420 | 2.383/2.385 |

*Plates are coated with recombinant huIL-17 (3 µg/ml) from E. coli (BM-E3141/98) or HEK/EBNA cells (En.E-3382/82). Supernatants are tested at the final dilution of ⅓.

Binding in ELISA of culture supernatants of the hybridoma clones: The reactivity in ELISA of the supernatants of the clones of the 11 hybridomas, which retained the best production of anti-huIL-17 MAb, is shown in Table 4. The clones, highlighted in bold, were selected for producing ~1 liter of supernatant in roller bottles for purification and analysis of the antibodies. With the exception of the clones derived from the hybridoma No 5, which produced a huIgG3κ antibody, all the other clones produced huIgG1κ MAb, as assessed by isotype specific monoclonal antibodies.

TABLE 4

ELISA reactivity of culture supernatants for hu-IL-17.

| Clone (No) | Supernatants* O.D. values |
|---|---|
| 3-2 | 2.198/1.940 |
| 3-20 | 1.909/1.939 |
| 3-21 | 1.873/1.812 |
| 5-18 | 1.240/1.168 |
| 5-22 | 1.340/1.396 |
| 5.29 | 1.316/1.354 |
| 5.31 | 1.227/1.302 |
| 5-40 | 1.364/1.543 |
| 104-2 | 1.385/1.299 |
| 104-4 | 1.085/1.044 |
| 104-9 | 1.488/1.304 |
| 104-11 | 1.670/1.380 |
| 106-1 | 1.244/1.306 |
| 106.2 | 1.203/1.138 |
| 106-3 | 1.176/1.166 |
| 110-7 | 1.535/1.393 |
| 110-28 | 1.376/1.370 |
| 305-21 | 1.484/1.518 |
| 305-38 | 1.669/1.858 |
| 343-1 | 1.351/1.375 |
| 439-80 | 2.506/2.543 |
| 450-13 | 1.568/1.610 |
| 450-23 | 1.658/1.667 |
| 543-1 | 1.074/0.991 |
| 543-4 | 1.003/0.913 |
| 543-16 | 0.795/0.717 |
| 557-6 | 0.879/0.940 |
| 557-36 | 0.980/0.925 |
| 557-37 | 1.104/1.109 |
| 622-2 | 0.923/0.894 |
| 622-5 | 1.070/1.032 |
| 622-6 | 0.980/0.953 |
| 658-2 | 0.744/0.744 |
| 658-6 | 0.769/0.772 |
| 658-16 | 0.741/0.758 |

Microtiter plates are coated with recombinant huIL-17 (3 µg/ml) from HEK/EBNA cells (En.E-3382/82).

Neutralizing activity of culture supernatants: Culture supernatants are tested for inhibition of huIL-6 production by human dermal fibroblasts stimulated with recombinant huIL-17. As shown in Table 5, the majority of the culture supernatants show inhibitory activity.

TABLE 5

Inhibition of IL-6 production induced by huIL-17 in human dermal fibroblasts by culture supernatants

| Clone (No) | Inhibition of IL-6 production (%) Amount of huIL-17 used as stimulus (ng/ml) | | | |
|---|---|---|---|---|
|  | 62.5 | 125 | 250 | 500 |
| 3-20 | 86.3 | 75.0 | 33.1 | 23.2 |
| 5-40 | 23.3 | 41.4 | 20.3 | 19.0 |
| 104-11 | 47.7 | 48.5 | 22.2 | 16.3 |
| 106.1 | 61.6 | 19.8 | 5.7 | 9.8 |
| 110-28 | 99.8 | 92.5 | 88.6 | 61.3 |
| 305-38 | 47.2 | 47.1 | 36.6 | 23.7 |
| 343-1 | 96.8 | 102.4 | 90.5 | 66.4 |
| 450-23 | 51.7 | 48.5 | 47.5 | 26.6 |
| 543.4 | −6.0 | −12.0 | −6.5 | −7.1 |
| 622-2 | 34.0 | 23.2 | 20.3 | 18.4 |
| 658-16 | 34.4 | 27.7 | 12.7 | 18.8 |

Neutralizing activity of AIN45: Selection of clone 110-28 for the production of development candidate AIN457 (preferred embodiment of the invention) is based on neutralizing activity and affinity measurement on BIACORE 2000 of the purified antibodies (see below Example 2).

Example 2

AIN457 Binds with Very High Affinity to Recombinant Human IL-17 (huIL-17); the $K_D$ is 122±22 pM (BIAcore) and Neutralizes Human IL-6 Production Induced by huIL-17 in Human Dermal Fibroblast; IC50 is 2.1±0.1 nM at a Concentration of 1.87 nM huIL-17 a) Methods

Reagents: General laboratory reagents are purchased from Merck or Sigma and are of the highest purity grade available; the sources of specialty reagents are detailed below.

Proteins: Monoclonal antibodies are generated by immunizing MEDAREX transgenic mice with recombinant human IL-17, and then following the standard procedure for producing cell lines, from which the secreted material could be purified by Protein A Sepharose chromatography [essentially as described in Example 1). AIN457 is stored as a sterile-filtered solution in 50 mM Na-citrate, pH 7.0, 140 mM NaCl at 4° C. The recombinant human AIN457 (batch KB03303A) is obtained in sterile stock solution of either 20 mM Na-citrate/40 mM phosphate buffer, pH 7, 150 mM NaCl or 20 mM acetic acid pH 5.5 adjusted with 1M Tris-base. Concentrations are usually in the range of 2 mg/ml and diluted to a final concentration of 5 µg/ml into BIA buffer (20 mM HEPES, pH 7.4, 150 mM NaCl, 0.05% v/v Tween-20) for the Biacore experiments. Recombinant human IL-17 is produced in-house; batch En/E 3882/83; 0.29 mg/ml.

BIAcore Measurements

Determination of kinetic binding parameters and levels of crossreactivity are done by surface plasmon resonance measurements using the optical biosensor BIAcore 2000 (BIAcore AB, Upsalla, Sweden, see Lit. HS 1,2 for details). This technology allows the label-free determination the microscopic rate constants for binding ($k_{on}$) and dissociation ($k_{off}$) of a ligand to a receptor. It is therefore especially suited for characterizing the antibody-antigen interactions. This technology complements and is in many respects superior to ELISA measurements (Van Regenmortel, Dev Biol (Basel). 2003; 112:141-51.). Binding studies of recombinant IL-17 to the IL-17 antibody AIN457 are performed in two ways. In the standard protocol, AIN457 is captured by an anti-human Fcγ antibody (Jackson Immunochemicals; Cat. No. 109-005-098) that is previously immobilized onto a CM-5 BIAcore sensor chip (Research grade). Covalent binding of Fcγ capture antibody is done with the 'Amine coupling kit' provided by BIAcore (BIAcore, Cat. No. BR-1000-50). Typically, 3000 RUs of capture antibody are attached to the activated dextran surface with a 30 µg/ml anti Fcγ antibody solution in 10 mM Ac buffer, pH 4.5 at a flow rate of 5 µl/min which lead to approximately 250 RUs of AIN457 immobilization. As a guideline, 1000 RUs correspond to a mass transfer of 1 ng/mm². Alternatively, IL-17 (Section 3.2; Table 4), AIN457 antibody is coupled directly to the chip surface without capture antibody. The results are compared to the protocol described in Table 9 (see below).

b) Results

Binding Kinetics of the IL-17/AIN457 Complex

The equilibrium dissociation constant $K_D$ allows some judgement about the stability of complexes, once formed in vivo. We have therefore determined kinetic constants for the binding of human IL-17 to the immobilized AIN457 antibody, and have derived the $K_D$ for the process from these data. Table 3 shows the summary of data obtained when the curves of 2 experiments are fitted to the Langmuir model using the BIAevaluation 3.0 software. Although the antibody is, of course, bivalent, the binding can be treated as a 1:1 event, with individual antibody binding sites displayed at the surface that become occupied by monomeric IL-17 molecules. This experiment shows both, the extremely fast association as well as the very slow dissociation kinetics of the antibody-chemokine complex. The best data fit is obtained when the sensorgrams are treated individually (rather than globally, as is suggested in the BIAevaluation.) Thus, after combining the titration series we obtain average values from 12 sensorgrams of $k_{on}=(4.1\pm0.1)\times10^5$ 1/M s; $k_{off}=(3.8\pm0.5)\times10^{-4}$ 1/s; and for $K_D=122\pm22$ pM.

TABLE 3

Kinetic constants for the 1:1 binding of rec human IL-17 to NVP-AIN457

| Conc [nM] | kon [1/Ms] | koff [1/s] | KD [M] | Exp. IL-314 |
|---|---|---|---|---|
| 2 | 3.31E+05 | 3.36E−05 | 1.02E−10 | Run 1 |
| 4 | 1.28E+05 | 3.78E−05 | 2.95E−10 | |
| 8 | 3.79E+05 | 1.86E−05 | 4.90E−11 | |
| 12 | 3.60E+05 | 3.00E−05 | 8.33E−11 | |
| 16 | 3.52E+05 | 5.70E−05 | 1.62E−10 | |
| 20 | 3.52E+05 | 4.15E−05 | 1.18E−10 | |
| 2 | 1.23E+06 | 1.97E−05 | 1.60E−11 | Run 2 |
| 4 | 4.11E+05 | 1.20E−05 | 2.92E−11 | |
| 8 | 3.78E+05 | 4.54E−05 | 1.20E−10 | |
| 12 | 3.46E+05 | 5.13E−05 | 1.48E−10 | |
| 16 | 3.17E+05 | 5.95E−05 | 1.88E−10 | |
| 20 | 3.34E+05 | 5.01E−05 | 1.50E−10 | |
| Mean | 4.10E+05 | 3.80E−05 | 1.22E−10 | n = 12 |
| SEM | 7.73E+04 | 4.51E−06 | 2.21E−11 | |

Mean $K_D$ calculated from individual entries (vertically), rather than by applying the equation $K_D = k_{off}/k_{on}$.

For the AIN457 produced in recombinant cells (KB03303A) affinity measurements are performed for the IL-17 cytokines from man, marmoset, rhesus and cynomolgous monkey, respectively. Experimental details of the Biacore measurements are the same as described above for MAB 110-28 antibody. Two independent runs testing 6 IL-17 concentrations in each run are performed. Concentrations for human IL-17 are 2, 4, 8, 12, 16, 20 nM and 10, 20, 30, 40, 50, 60 nM for all other species. Complete data analysis yields n=12 individual measurements for each IL-17 species. The $K_D$ as well as SEM is reported.

TABLE 4

Summary: Kinetic constants for the 1:1 binding of rec human, marmoset, rhesus and cynomolgous monkey IL-17 to NVP-AIN457 (KB03303A)

| Species | KD [M] Mean Run 1 + 2 | SEM |
|---|---|---|
| Human | 0.227 nM | +/−0.03 nM |
| Marmoset | 1.2 nM | +/−0.1 nM |
| Rhesus monkey | 9 nM | +/−1 nM |
| Cynomolgous monkey | 6 nM | +/−0.7 nM |

A full set data of the BIAcore analysis for antibody KB03303A with $k_{on}$, $k_{off}$ and $K_D$ and the respective IL-17 species are given below in tables 5 to 8.

TABLE 5

Kinetic constants for the 1:1 binding of rec human IL-17 to AIN457 (KB03303A)

| Conc [nM] | kon [1/Ms] | koff [1/s] | KD [M] | Exp. IL-366/ IL-365 |
|---|---|---|---|---|
| 2 | 3.37E+05 | 6.43E−05 | 1.91E−10 | Run 1 |
| 4 | 2.59E+05 | 7.76E−05 | 2.99E−10 | |
| 8 | 2.12E+05 | 5.21E−05 | 2.46E−10 | |
| 12 | 2.18E+05 | 7.38E−05 | 3.38E−10 | |
| 16 | 2.02E+05 | 7.15E−05 | 3.54E−10 | |
| 20 | 1.92E+05 | 8.04E−05 | 4.20E−10 | |
| 2 | 5.50E+05 | 7.01E−05 | 1.27E−10 | Run 2 |
| 4 | 3.22E+05 | 3.30E−05 | 1.02E−10 | |
| 8 | 2.85E+05 | 4.73E−05 | 1.66E−10 | |
| 12 | 2.86E+05 | 4.84E−05 | 1.69E−10 | |
| 16 | 2.61E+05 | 3.09E−05 | 1.18E−10 | |
| 20 | 2.58E+05 | 4.90E−05 | 1.90E−10 | |
| Mean | 2.82E+05 | 5.82E−05 | 2.27E−10 | n = 12 |
| SEM | 2.77E+04 | 4.91E−06 | 3.00E−11 | |

TABLE 6

Kinetic constants for the 1:1 binding of rec marmoset IL-17 to AIN457 (KB03303A)

| Conc [nM] | kon [1/Ms] | koff [1/s] | KD [M] | Exp. IL-366/ IL-365 |
|---|---|---|---|---|
| 10 nM | 8.89E+04 | 7.96E−05 | 8.95E−10 | Run 1 |
| 20 nM | 1.11E+05 | 8.69E−05 | 7.82E−10 | |
| 30 nM | 9.82E+04 | 1.15E−04 | 1.17E−09 | |
| 40 nM | 9.92E+04 | 1.16E−04 | 1.17E−09 | |
| 50 nM | 9.81E+04 | 1.19E−04 | 1.21E−09 | |
| 10 nM | 8.83E+04 | 9.98E−05 | 1.13E−09 | Run 2 |
| 20 nM | 1.10E+05 | 1.28E−04 | 1.17E−09 | |
| 30 nM | 9.70E+04 | 1.52E−04 | 1.57E−09 | |
| 40 nM | 9.66E+04 | 1.31E−04 | 1.36E−09 | |
| 50 nM | 9.52E+04 | 1.59E−04 | 1.67E−09 | |
| Mean | 9.83E+04 | 1.19E−04 | 1.21E−09 | n = 10 |
| SEM | 2.36E+03 | 8.09E−06 | ±0.1 | |

TABLE 7

Kinetic constants for the 1:1 binding of rec rhesus monkey IL-17 to AIN457 (KB03303A)

| Conc [nM] | kon [1/Ms] | koff [1/s] | KD [M] | Exp. IL-366/ IL-365 |
|---|---|---|---|---|
| 10 | 1.70E+05 | 3.89E−04 | 2.28E−09 | Run 1 |
| 20 | 6.73E+04 | 4.94E−04 | 7.34E−09 | |
| 30 | 5.86E+04 | 3.54E−04 | 6.04E−09 | |
| 40 | 3.27E+04 | 4.05E−04 | 1.24E−08 | |
| 50 | 4.05E+04 | 4.55E−04 | 1.12E−08 | |
| 60 | 3.50E+04 | 4.60E−04 | 1.31E−08 | |
| 10 | 5.47E+04 | 3.85E−04 | 7.04E−09 | Run 2 |
| 20 | 4.62E+04 | 2.74E−04 | 5.93E−09 | |
| 30 | 4.30E+04 | 3.51E−04 | 8.16E−09 | |
| 40 | 3.76E+04 | 3.66E−04 | 9.74E−09 | |
| 50 | 3.60E+04 | 4.32E−04 | 1.20E−08 | |
| 60 | 3.44E+04 | 4.24E−04 | 1.23E−08 | |
| Mean | 5.47E+04 | 3.99E−04 | 8.96E−09 | n = 12 |
| SEM | 1.09E+04 | 1.72E−05 | 9.70E−10 | |

TABLE 8

Kinetic constants for the 1:1 binding of rec cynomolgous monkey IL-17 to AIN457 (KB03303A)

| Conc [nM] | kon [1/Ms] | koff [1/s] | KD [M] | Exp. IL-366/IL-365 |
|---|---|---|---|---|
| 5 nM | 3.27E+05 | 3.60E−04 | 1.10E−09 | Run 1 |
| 10 nM | 1.79E+05 | 4.02E−04 | 2.24E−09 | |
| 15 nM | 1.03E+05 | 5.67E−04 | 5.50E−09 | |
| 20 nM | 1.10E+05 | 5.23E−04 | 4.75E−09 | |
| 25 nM | 9.23E+04 | 5.78E−04 | 6.26E−09 | |
| 30 nM | 9.05E+04 | 7.14E−04 | 7.89E−09 | |
| 5 nM | 7.18E+04 | 5.08E−04 | 7.08E−09 | Run 2 |
| 10 nM | 9.70E+04 | 6.69E−04 | 6.90E−09 | |
| 15 nM | 1.03E+05 | 7.66E−04 | 7.41E−09 | |
| 20 nM | 1.02E+05 | 7.32E−04 | 7.17E−09 | |
| 25 nM | 1.02E+05 | 7.47E−04 | 7.34E−09 | |
| 30 nM | 1.00E+05 | 8.34E−04 | 8.32E−09 | |
| Mean | 1.23E+05 | 6.17E−04 | 6.00E−09 | n = 10 |
| SEM | 1.99E+04 | 4.34E−05 | 6.52E−10 | |

Subsequently inhibitory activity of purified AIN457 (Batch En/E-10333/53; 0.54 mg/ml) on huIL-17 is evaluated. $IC_{50}$ values are shown in Table 6. In these experiments, huIL-17R/Fc and a mouse anti-huIL-17 MAb are included as positive controls and Simulect as negative control.

TABLE 9

Neutralization of hu-IL-17 by the human anti-huIL-17 MAb AIN457 in comparison with IL-17R/Fc, and a mouse anti-huIL-17 MAb (R&D System).

| | AIN457 $IC_{50}$ ± SEM (n = 3*) | IL-17 R/Fc $IC_{50}$ ± SEM (n = 3) | MAB 317 $IC_{50}$ ± SEM (n = 3) |
|---|---|---|---|
| Recombinant huIL-17 @ 1.87 nM (30 ng/ml) | 2.071 ± 0.116 nM | 1.713 ± 0.305 nM | 12.226 ± 2.050 nM |

*Means and SEM are calculated from three different and independent experiments.

In conclusion, AIN457 abrogates the IL-17-dependent secretion of huIL-6 by human dermal fibroblasts. The potency is comparable to that of huIL-17R/Fc and superior to that of a commercially available mouse anti-huIL-17 MAb. It is interesting to note that a more complete inhibition is observed with AIN457 than with IL-17R/Fc.

Example 3

Purity and Partial Amino Acid Sequences of Heavy and Light Chain Amino Acid Sequencing Amino-terminal amino acid sequences of $V_L$ and $V_H$ regions: The first 48 amino-acid residues of the heavy and the light chain for two anti-IL-17A antibodies, clone 110-7 (see table 4) and 110-28 (see table 4), are determined by Edman degradation. The amino-acid sequence is identical for both clones. The GeneBank is searched by blast analysis and the most homologous DNA sequence found is used to design the cloning primers.

Molecular cloning of the VL and VH regions: Total RNA is prepared from $2\times10^7$ hybridoma cells (clone 110-7, clone 110-28) with the RNeasy Midi Kit according to the vendor's protocol (Quiagen Hilden Germany). Total RNA is eluted in 200 µl RNase-free water and stored at −80° C. The first strand cDNA synthesis is carried out with M-MLV reverse transcriptase (Promega, Madison, Wis.), oligo-dT primer, PCR nucleotide mix (dNTPs) and RNAsin inhibitor (Roche, Mannheim). Five µg of total RNA is mixed with 1 µl oligo-dT primer (0.5 µg/µl), and RNase-free water is added to a final volume of 36 µl. The mixture is incubated at 70° C. for 10 minutes and then stored on ice. While on ice, the following reagents are added: 10 µl 5×RT buffer, 2 µl dNTPs (10 mM each), 2 µl RNasin and 1 µl M-MLV reverse transcriptase. The reaction is carried out at 42° C. for 1 hour.

The PCR reaction is assembled using 4 µl of cDNA template, 2 µl of each primer at 10 µM each (see below and Tables 10 and 11 for overview) 20 µl of 2× Qiamix (containing Buffer, dNTP's, TAQPolymerase) and 1 µl of Pwo DNA polymerase in a total volume of 40 µl. The PCR conditions are set for 35 cycles of 94° C. for 15 seconds, 55° C. for 20 seconds and 72° C. for 30 seconds. The PCR product is subcloned into the pCR4-TOPO-Zero (Stragagene, La Jolla, Calif.) cloning vector. Several clones are picked from each reaction and the nucleotide sequence determined by Solvias AG (Basel), using the primers MV432 (SEQ ID NO: 21), MV433 (SEQ ID NO: 22), MV434 (SEQ ID NO: 23), MV435 (SEQ ID NO: 14), and standard primers in the vector DNA.

The cDNA encoding the heavy chain is amplified using the primer pairs MV416 (SEQ ID NO: 15)/#265 (SEQ ID NO: 16) and MV418 (SEQ ID NO: 17)/#265 (SEQ ID NO: 16). The primers cover the nucleotide sequences corresponding to the following amino acid positions of the heavy chain: MV416 position −19/−13 (signal peptide); MV418 position +1/+7; #265 position +253/+259. Position +1 is the first amino acid of the mature protein.

The cDNA encoding the light chain is amplified using the primer pairs MV417 (SEQ ID NO: 18)/#223 (SEQ ID NO: 19) and MV419 (SEQ ID NO: 20)/#223 (SEQ ID NO: 19). The primers cover the nucleotide sequences corresponding to the following amino-acid positions of the light chain: MV417 position −20/−14 (signal peptide); MV419 position +1/+7; #223 position +210/+215. This approach permitted to make two independent PCR amplifications for each immunoglobulin chain, resulting in two independently established DNA sequences.

Results and Discussion

The cloned PCR products coding for the heavy and light chain from two hybridomas (110-7 and 110-28, see Table 4 above) are characterized by DNA sequencing. Five and six independent sequences are used to assemble the light and heavy chain sequences. The light chain cDNAs are all identical and covere the entire coding sequence (amino acid position −20 to +215). The heavy chain cDNAs had 2 different mismatches in one cDNA each. These are excluded from the final sequence, which extends from the initiation codon to the end of the hinge region after the constant domain 1 (amino acid position −19 to +238). The sequences for both hybridomas are identical. The cDNA obtained from hybridoma 110-28 is selected and used for all further expression work. SEQ ID NO: 7 (cDNA of heavy chain of AIN457), SEQ ID NO: 8 (amino acid sequence of heavy chain of AIN457), SEQ ID NO: 9 (cDNA of light chain of AIN457) and SEQ ID NO: 10 (amino acid sequence of AIN457) show the DNA sequence coding for the light and heavy chain of AIN457, along with the protein sequence and the position of the primers used for PCR amplification and DNA sequencing. The DNA sequences have been registered in PlasNova, accession number NPL003689 for the heavy chain, and accession number NPL003690 for the light chain.

The amino acid sequence found by cDNA cloning is identical to that previously obtained by Edman degradation of the purified immunoglobulin heavy and light chains, indicating that the correct cDNA has been cloned.

TABLE 10

Nucleotide and amino-acid sequence of the light chain

The amino-acid sequence coding for the variable domain is bold and underlined. The oligonucleotide primers used for cloning are indicated (underlined).

```
SEQ ID NO:24  MV417    ACCATGGAAACCCCAGCGGAGCTTCTCTTCCTCCTGCTACTCTGGCTCCCAGATACCACC
                     1 ---------+---------+---------+---------+---------+---------+   60
SEQ ID NO:26           TGGTACCTTTGGGGTCGCCTCGAAGAGAAGGAGGACGATGAGACCGAGGGTCTATGGTGG
SEQ ID NO:25           T  M  E  T  P  A  E  L  L  F  L  L  L  W  L  P  D  T  T       -

MV419    GGAGAAATTGTGTTGACGCAGTCTCCAGGCACCCTGTCTTTGTCTCCAGGGGAAAGAGCC
                    61 ---------+---------+---------+---------+---------+---------+  120
                       CCTCTTTAACACAACTGCGTCAGAGGTCCGTGGGACAGAAACAGAGGTCCCCTTTCTCGG
                       G  E  I  V  L  T  Q  S  P  G  T  L  S  L  S  P  G  E  R  A   -

ACCCTCTCCTGCAGGGCCAGTCAGAGTGTTAGCAGCAGCTACTTAGCCTGGTACCAGCAG
                   121 ---------+---------+---------+---------+---------+---------+  180
                       TGGGAGAGGACGTCCCGGTCAGTCTCACAATCGTCGTCGATGAATCGGACCATGGTCGTC
                       T  L  S  C  R  A  S  Q  S  V  S  S  S  Y  L  A  W  Y  Q  Q   -

AAACCTGGCCAGGCTCCCAGGCTCCTCATCTATGGTGCATCCAGCAGGGCCACTGGCATC
                   181 ---------+---------+---------+---------+---------+---------+  240
                       TTTGGACCGGTCCGAGGGTCCGAGGAGTAGATACCACGTAGGTCGTCCCGGTGACCGTAG
                       K  P  G  Q  A  P  R  L  L  I  Y  G  A  S  S  R  A  T  G  I   -

CCAGACAGGTTCAGTGGCAGTGGGTCTGGGACAGACTTCACTCTCACCATCAGCAGACTG
                   241 ---------+---------+---------+---------+---------+---------+  300
                       GGTCTGTCCAAGTCACCGTCACCCAGACCCTGTCTGAAGTGAGAGTGGTAGTCGTCTGAC
                       P  D  R  F  S  G  S  G  S  G  T  D  F  T  L  T  I  S  R  L   -

GAGCCTGAAGATTTTGCAGTGTATTACTGTCAGCAGTATGGTAGCTCACCGTGCACCTTC
                   301 ---------+---------+---------+---------+---------+---------+  360
                       CTCGGACTTCTAAAACGTCACATAATGACAGTCGTCATACCATCGAGTGGCACGTGGAAG
                       E  P  E  D  F  A  V  Y  Y  C  Q  Q  Y  G  S  S  P  C  T  F   -

GGCCAAGGGACACGACTGGAGATTAAACGAACTGTGGCTGCACCATCTGTCTTCATCTTC
                   361 ---------+---------+---------+---------+---------+---------+  420
                       CCGGTTCCCTGTGCTGACCTCTAATTTGCTTGACACCGACGTGGTAGACAGAAGTAGAAG
                       G  Q  G  T  R  L  E  I  K  R  T  V  A  A  P  S  V  F  I  F   -

CCGCCATCTGATGAGCAGTTGAAATCTGGAACTGCCTCTGTTGTGTGCCTGCTGAATAAC
                   421 ---------+---------+---------+---------+---------+---------+  480
                       GGCGGTAGACTACTCGTCAACTTTAGACCTTGACGGAGACAACACACGGACGACTTATTG
                       P  P  S  D  E  Q  L  K  S  G  T  A  S  V  V  C  L  L  N  N   -

TTCTATCCCAGAGAGGCCAAAGTACAGTGGAAGGTGGATAACGCCCTCCAATCGGGTAAC
                   481 ---------+---------+---------+---------+---------+---------+  540
                       AAGATAGGGTCTCTCCGGTTTCATGTCACCTTCCACCTATTGCGGGAGGTTAGCCCATTG
                       F  Y  P  R  E  A  K  V  Q  W  K  V  D  N  A  L  Q  S  G  N   -

TCCCAGGAGAGTGTCACAGAGCAGGACAGCAAGGACAGCACCTACAGCCTCAGCAGCACC
                   541 ---------+---------+---------+---------+---------+---------+  600
                       AGGGTCCTCTCACAGTGTCTCGTCCTGTCGTTCCTGTCGTGGATGTCGGAGTCGTCGTGG
                       S  Q  E  S  V  T  E  Q  D  S  K  D  S  T  Y  S  L  S  S  T   -

CTGACGCTGAGCAAAGCAGACTACGAGAAACACAAAGTCTACGCCTGCGAAGTCACCCAT
                   601 ---------+---------+---------+---------+---------+---------+  660
                       GACTGCGACTCGTTTCGTCTGATGCTCTTTGTGTTTCAGATGCGGACGCTTCAGTGGGTA
                       L  T  L  S  K  A  D  Y  E  K  H  K  V  Y  A  C  E  V  T  H   -

CAGGGCCTGAGCTCGCCCGTCACAAAGAGCTTCAACAGGGGAGAGTGTTAG
                   661 ---------+---------+---------+---------+---------+-            711
                       GTCCCGGACTCGAGCGGGCAGTGTTTCTCGAAGTTGTCCCCTCTCACAATC
                       Q  G  L  S  S  P  V  T  K  S  F  N  R  G  E  C  *            -
```

TABLE 11

Nucleotide and amino-acid sequence of the heavy chain

The amino-acid sequence coding for the variable domain is bold and underlined. The oligonucleotide primers used for cloning and sequencing are indicated.

```
SEQ ID NO:27  MV416    ACCATGGAATTGGGGCTGAGCTGGGTTTTCCTTGTTGCTATTTTAGAAGGTGTCCACTGT
                     1 ---------+---------+---------+---------+---------+---------+   60
```

TABLE 11-continued

Nucleotide and amino-acid sequence of the heavy chain

The amino-acid sequence coding for the variable domain is bold and underlined. The oligonucleotide primers used for cloning and sequencing are indicated.

```
SEQ ID NO:29           TGGTACCTTAACCCCGACTCGACCCAAAAGGAACAACGATAAAATCTTCCACAGGTGACA
SEQ ID NO:28            T  M  E  L  G  L  S  W  V  F  L  V  A  I  L  E  G  V  H  C    -

MV418         GAGGTGCAGTTGGTGGAGTCTGGGGGAGGCTTGGTCCAGCCTGGGGGGTCCCTGAGACTC
                   61 ---------+---------+---------+---------+---------+---------+  120
                      CTCCACGTCAACCACCTCAGACCCCCTCCGAACCAGGTCGGACCCCCCAGGGACTCTGAG
                       E  V  Q  L  V  E  S  G  G  G  L  V  Q  P  G  G  S  L  R  L    -

TCCTGTGCAGCCTCTGGATTCACCTTTAGTAACTATTGGATGAACTGGGTCCGCCAGGCT
                  121 ---------+---------+---------+---------+---------+---------+  180
                      AGGACACGTCGGAGACCTAAGTGGAAATCATTGATAACCTACTTGACCCAGGCGGTCCGA
                       S  C  A  A  S  G  F  T  F  S  N  Y  W  M  N  W  V  R  Q  A    -

CCAGGGAAAGGGCTGGAGTGGGTGGCCGCCATAAACCAAGATGGAAGTGAGAAATACTAT
                  181 ---------+---------+---------+---------+---------+---------+  240
                      GGTCCCTTTCCCGACCTCACCCACCGGCGGTATTTGGTTCTACCTTCACTCTTTATGATA
                       P  G  K  G  L  E  W  V  A  A  I  N  Q  D  G  S  E  K  Y  Y    -

GTGGGCTCTGTGAAGGGCCGATTCACCATCTCCAGAGACAACGCCAAGAACTCACTGTAT
                  241 ---------+---------+---------+---------+---------+---------+  300
                      CACCCGAGACACTTCCCGGCTAAGTGGTAGAGGTCTCTGTTGCGGTTCTTGAGTGACATA
                       V  G  S  V  K  G  R  F  T  I  S  R  D  N  A  K  N  S  L  Y    -

MV432         CTGCAAATGAACAGCCTGAGAGTCGAGGACACGGCTGTGTATTACTGTGTGAGGGACTAT
                  301 ---------+---------+---------+---------+---------+---------+  360
                      GACGTTTACTTGTCGGACTCTCAGCTCCTGTGCCGACACATAATGACACACTCCCTGATA
                       L  Q  M  N  S  L  R  V  E  D  T  A  V  Y  Y  C  V  R  D  Y    -

TACGATATTTTGACCGATTATTACATCCACTATTGGTACTTCGATCTCTGGGGCCGTGGC
                  361 ---------+---------+---------+---------+---------+---------+  420
                      ATGCTATAAAACTGGCTAATAATGTAGGTGATAACCATGAAGCTAGAGACCCCGGCACCG
                       Y  D  I  L  T  D  Y  Y  I  H  Y  W  Y  F  D  L  W  G  R  G    -

MV433         ACCCTGGTCACTGTCTCCTCAGCCTCCACCAAGGGCCCATCGGTCTTCCCCCTGGCACCC
                  421 ---------+---------+---------+---------+---------+---------+  480
         MV434         TGGGACCAGTGACAGAGGAGTCGGAGGTGGTTCCCGGGTAGCCAGAAGGGGGACCGTGGG
                       T  L  V  T  V  S  S  A  S  T  K  G  P  S  V  F  P  L  A  F    -

TCCTCCAAGAGCACCTCTGGGGGCACAGCGGCCCTGGGCTGCCTGGTCAAGGACTACTTC
                  481 ---------+---------+---------+---------+---------+---------+  540
                      AGGAGGTTCTCGTGGAGACCCCCGTGTCGCCGGGACCCGACGGACCAGTTCCTGATGAAG
                       S  S  K  S  T  S  G  G  T  A  A  L  G  C  L  V  K  D  Y  F    -

CCCGAACCGGTGACGGTGTCGTGGAACTCAGGCGCCCTGACCAGCGGCGTGCACACCTTC
                  541 ---------+---------+---------+---------+---------+---------+  600
                      GGGCTTGGCCACTGCCACAGCACCTTGAGTCCGCGGGACTGGTCGCCGCACGTGTGGAAG
                       P  E  P  V  T  V  S  W  N  S  G  A  L  T  S  G  V  H  T  F    -

CCGGCTGTCCTACAGTCCTCAGGACTCTACTCCCTCAGCAGCGTGGTGACCGTGCCCTCC
                  601 ---------+---------+---------+---------+---------+---------+  660
                      GGCCGACAGGATGTCAGGAGTCCTGAGATGAGGGAGTCGTCGCACCACTGGCACGGGAGG
                       P  A  V  L  Q  S  S  G  L  Y  S  L  S  S  V  V  T  V  P  S    -

AGCAGCTTGGGCACCCAGACCTACATCTGCAACGTGAATCACAAGCCCAGCAACACCAAG
                  661 ---------+---------+---------+---------+---------+---------+  720
         MV435         TCGTCGAACCCGTGGGTCTGGATGTAGACGTTGCACTTAGTGTTCGGGTCGTTGTGGTTC
                       S  S  L  G  T  Q  T  Y  I  C  N  V  N  H  K  P  S  N  T  K    -

GTGGACAAGAGAGTTGAGCCCAAATCTTGTGACAAAACTCACACATGCCCACCGTGCCCA
                  721 ---------+---------+---------+---------+---------+---------+  780
                      CACCTGTTCTCTCAACTCGGGTTTAGAACACTGTTTTGAGTGTGTACGGGTGGCACGGGT
                       V  D  K  R  V  E  P  K  S  C  D  K  T  H  T  C  P  P  C  P    -

TAA
                  781 ---                                                            783
                      ATT
                       *
```

Example 4

Three-Dimensional Structure of the Fab Fragment of the Anti Human IL-17A Monoclonal Antibody AIN457

In order to determine the conformation of the Complementarity-Determining Regions (CDR's) and the structure of the antigen-binding site of AIN457, the Fab fragment is generated, crystallized and its X-ray structure is determined by protein crystallography.

Method: The Fab fragment of NVP-AIN457 is produced by papain cleavage from the whole antibody and purified by protein A chromatography followed by size-exclusion chromatography. The purified material is then concentrated by ultrafiltration to 20 mg/ml in 10 mM Tris-HCl pH 7.4, 25 mM NaCl, 5 mM TCEP. Crystals are grown by the technique of vapor diffusion in hanging drops at 19° C., from 2.0 M ammonium sulfate, 5% PEG 400, 0.1M Na MES pH 6.5. They are in space group $P2_12_12_1$ with unit cell dimensions a=90.3 Å, b=106.7 Å, c=131.4 Å and 2 Fab molecules per asymmetric unit. Prior to X-ray data collection, a single crystal of AIN457 Fab is cross-linked with glutaraldehyde using the method of Lusty (J. Appl. Cryst. (1999) 32, 106-112) and then transferred to a solution containing 2.0M $Li_2SO_4$, 2% PEG 400, and 0.1M Na MES pH 6.5. The crystal is subsequently mounted in a cryo-loop and flash-frozen for data collection at 95K. 180 diffraction images corresponding to 1.0 deg oscillation each are recorded. The diffraction data are processed with the HKL program suite. The structure is determined to 2.5 Å resolution by molecular replacement. The structure is then refined by torsion angle dynamics and energy minimization using the program CNX.

Results: Two AIN457 Fab molecules are present in the asymmetric unit of the crystal, with the H-CDR3 loop of both Fab molecules involved in protein-protein contacts to the H-CDR3 loop of symmetry-related Fabs. The two Fab molecules show different elbow angles but have otherwise essentially identical CDR loop conformations (see Table 12 for amino acid sequence of the CDR loops). The H-CDR1 loop adopts the expected H1:1 canonical structure, while the conformation of the H-CDR2 loop matches that of canonical structure H2:3A. The H-CDR3 loop of the AIN457 antibody is exceptionally long, comprising 18 residues between Kabat positions 94 (Arg H98) and 101 (Asp H115). It shows the typical bulged torso structure stabilized by a salt bridge between the Arg side-chain in position 94 (Arg H98) and the Asp carboxylate group in position H101 (Asp H115), and by an H-bonded interaction between the side-chain of Trp H117 and the main-chain carbonyl group of Phe H114. The head of the H-CDR3 loop has the structure of a long, twisted beta-hairpin with a second beta-bulge at its base and a type I' beta-turn at its apex. A striking feature of the AIN457 H-CDR3 loop is its very high content in aromatic residues: 6 tyrosines, 2 tryptophanes, 1 phenylalanine. Since all other CDR loops contribute 1 more tyrosine each, the antigen-combining site of AIN457 possesses 11 tyrosines in total. The conformations of the L-CDR1 and L-CDR2 loops correspond to canonical structures L1:6 and L2:1, respectively. In contrast to H-CDR3, the L-CDR3 loop is short (6 residues) and shows the commonly observed canonical structure L3:1, with a cis-proline at its tip (Pro L96), a glutamine at Kabat position 90 (Gln L91) and a threonine at Kabat position 97 (Thr L98). However, a very unusual feature of the AIN457 L-CDR3 loop is the presence of a cysteine residue after the cis-proline (Cys L97). The side-chain of Cys L97 is at the bottom of a shallow depression located at the $V_L$-$V_H$ interface and lined by residues Trp H112, Trp H47 and Tyr L92.

TABLE 12

| Light-chain | | |
|---|---|---|
| L-CDR1 | Kabat definition | R-A-S-Q-S-V-S-S-S-Y-L-A (SEQ ID NO: 4) |
| | Chothia/X-ray definition | R-A-S-Q-S-V-S-S-S-Y-L-A (SEQ ID NO: 4) |
| L-CDR2 | Kabat definition | G-A-S-S-R-A-T (SEQ ID NO: 5) |
| | Chothia/X-ray definition | G-A-S-S-R-A-T (SEQ ID NO: 5) |
| L-CDR3 | Kabat definition | Q-Q-Y-G-S-S-P-C-T (SEQ ID NO: 6) |
| | Chothia/X-ray definition | Q-Q-Y-G-S-S-P-C-T (SEQ ID NO: 6) |

| Heavy-chain | | |
|---|---|---|
| H-CDR1 | Kabat definition | N-Y-W-M-N (SEQ ID NO: 1) |
| | Chothia/X-ray definition | G-F-T-F-S-N-Y-W-M-N (SEQ ID NO: 11) |
| H-CDR2 | Kabat definition | A-I-N-Q-D-G-S-E-K-Y-Y-V-G-S-V-K-G (SEQ ID NO: 2) |
| | Chothia/X-ray definition | A-I-N-Q-D-G-S-E-K-Y-Y (SEQ ID NO: 12) |
| H-CDR3 | Kabat definition | D-Y-Y-D-I-L-T-D-Y-Y-I-H-Y-W-Y-F-D-L (SEQ ID NO: 3) |
| | Chothia/X-ray definition | C-V-R-D-Y-Y-D-I-L-T-D-Y-Y-I-H-Y-W-Y-F-D-L-W-G (SEQ ID NO: 13) |

Amino acid sequences of the hypervariable regions of the AIN457 monoclonal antibodies, based on the Kabat definition and as determined by the X-ray analysis, using the approach of Chothia and coworkers. Amino acid highlighted in bold are part of the CDR loops, while those shown in plain style are part of the antibody framework.

---

The invention claimed is:

1. A purified IL-17 binding molecule comprising a heavy chain variable domain comprising SEQ ID NO:8.

2. A purified IL-17 binding molecule comprising a light chain variable domain comprising SEQ ID NO:10.

3. A purified IL-17 binding molecule comprising a heavy chain variable domain comprising SEQ ID NO:8 and a light chain variable domain comprising SEQ ID NO:10.

4. A purified IL-17 binding molecule comprising a heavy chain variable domain comprising the three Complementarity-Determining Regions (CDRs) of SEQ ID NO:8 and a light chain variable domain comprising the three CDRs of SEQ ID NO:10.

5. The purified IL-17 binding molecule of claim 4, wherein said three CDRs of SEQ ID NO:8 are set forth in SEQ ID NO:1, SEQ ID NO:2 and SEQ ID NO:3.

6. The purified IL-17 binding molecule of claim 4, wherein said three CDRs of SEQ ID NO:8 are set forth in SEQ ID NO:11, SEQ ID NO:12 and SEQ ID NO:13.

7. The purified IL-17 binding molecule of claim 5, wherein said three CDRs of SEQ ID NO:10 are set forth in SEQ ID NO:4, SEQ ID NO:5 and SEQ ID NO:6.

8. The purified IL-17 binding molecule of claim 6, wherein said three CDRs of SEQ ID NO:10 are set forth in SEQ ID NO:4, SEQ ID NO:5 and SEQ ID NO:6.

9. The purified IL-17 binding molecule of either claim 7 or 8, wherein said IL-17 binding molecule is a human antibody.

10. A pharmaceutical composition comprising the purified IL-17 binding molecule of either claim 7 or 8 and a pharmaceutically acceptable diluent, excipient, carrier or mixture thereof.

11. A pharmaceutical composition comprising the purified IL-17 binding molecule of claim 9 and a pharmaceutically acceptable diluent, excipient, carrier or mixture thereof.

12. A method for inhibiting the binding of IL-17 to an IL-17 receptor in a subject, comprising administering to the subject the purified IL-17 binding molecule of either claim 7 or 8 in an amount effective to inhibit the binding of IL-17 to the IL-17 receptor in the subject.

13. A method for inhibiting the binding of IL-17 to an IL-17 receptor in a subject, comprising administering to the subject the purified IL-17 binding molecule of claim 9 in an amount effective to inhibit the binding of IL-17 to the IL-17 receptor in the subject.

14. A method for inhibiting the binding of IL-17 to an IL-17 receptor in a subject, comprising administering to the subject the pharmaceutical composition of claim 11 in an amount effective to inhibit the binding of IL-17 to the IL-17 receptor in the subject.

15. A method for binding IL-17 in a subject, comprising administering to the subject the purified IL-17 binding molecule of either claim 7 or 8 in an amount effective to bind IL-17 in the subject.

16. A method for binding IL-17 in a subject, comprising administering to the subject the purified IL-17 binding molecule of claim 9 in an amount effective to bind IL-17 in the subject.

17. A method for binding IL-17 in a subject, comprising administering to the subject the pharmaceutical composition of claim 11 in an amount effective to bind IL-17 in the subject.

18. A method for treating an IL-17 mediated inflammatory condition or IL-17 mediated autoimmune disease in a subject, comprising administering to the subject in need thereof an effective amount of the purified IL-17 binding molecule of either claim 7 or 8.

19. A method for treating an IL-17 mediated inflammatory condition or IL-17 mediated autoimmune disease in a subject, comprising administering to the subject in need thereof an effective amount of the purified IL-17 binding molecule of claim 9.

20. A method for treating an IL-17 mediated inflammatory condition or IL-17 mediated autoimmune disease in a subject, comprising administering to the subject in need thereof an effective amount of the pharmaceutical composition of claim 11.

21. The method according to claim 19, wherein said IL-17 mediated inflammatory condition or autoimmune disease is rheumatoid arthritis.

22. The method according to claim 19, wherein said IL-17 mediated inflammatory condition or autoimmune disease is psoriasis.

* * * * *